US012644007B2

(12) United States Patent
Prouvost et al.

(10) Patent No.: US 12,644,007 B2
(45) Date of Patent: Jun. 2, 2026

(54) OXIRANE-FUNCTIONAL VINYL MONOMERS AND METHODS FOR MAKING THE SAME

(71) Applicant: SWIMC LLC, Cleveland, OH (US)

(72) Inventors: Benoit Prouvost, Nantes (FR); Matthieu Andriot, Attignat (FR)

(73) Assignee: SWIMC LLC, Cleveland, OH (US)

( * ) Notice: Subject to any disclaimer, the term of this patent is extended or adjusted under 35 U.S.C. 154(b) by 1097 days.

(21) Appl. No.: 17/586,167

(22) Filed: Jan. 27, 2022

(65) Prior Publication Data

US 2022/0145114 A1 May 12, 2022

Related U.S. Application Data

(63) Continuation-in-part of application No. PCT/US2021/035397, filed on Jun. 2, 2021.

(60) Provisional application No. 63/034,208, filed on Jun. 3, 2020.

(51) Int. Cl.

| | |
|---|---|
| ***B01J 31/02*** | (2006.01) |
| ***B65D 65/42*** | (2006.01) |
| ***C07D 303/24*** | (2006.01) |
| ***C08F 212/08*** | (2006.01) |
| ***C08F 220/06*** | (2006.01) |
| ***C08F 220/40*** | (2006.01) |
| ***C09D 125/14*** | (2006.01) |
| ***C09D 133/10*** | (2006.01) |

(52) U.S. Cl.

CPC ........ *C09D 125/14* (2013.01); *B01J 31/0239* (2013.01); *B65D 65/42* (2013.01); *C07D 303/24* (2013.01); *C08F 212/08* (2013.01); *C08F 220/06* (2013.01); *C08F 220/40* (2013.01); *C09D 133/10* (2013.01)

(58) Field of Classification Search

CPC .. B01J 31/0239; C07D 303/24; C09D 125/14; C08F 212/08; C08F 220/06; C08F 220/40

See application file for complete search history.

(56) References Cited

U.S. PATENT DOCUMENTS

| | | | |
|---|---|---|---|
| 7,189,787 | B2 | 3/2007 | O'Brien et al. |
| 9,862,854 | B2 | 1/2018 | O'Brien et al. |
| 2002/0155235 | A1 | 10/2002 | Taylor et al. |
| 2013/0316109 | A1 | 11/2013 | Niederst et al. |
| 2017/0210689 | A1 | 7/2017 | Reno et al. |
| 2020/0048301 | A1 | 2/2020 | Bassett et al. |
| 2021/0147692 | A1 | 5/2021 | Joslin et al. |

FOREIGN PATENT DOCUMENTS

| | | | |
|---|---|---|---|
| JP | 1-102072 | A | 4/1989 |
| WO | WO 03/022944 | A1 | 3/2003 |
| WO | WO 2014/089410 | A1 | 6/2014 |
| WO | WO 2014/186285 | A1 | 11/2014 |
| WO | WO 2015/002961 | A1 | 1/2015 |
| WO | WO 2017/007883 | A1 | 1/2017 |
| WO | WO 2017/112837 | A1 | 6/2017 |
| WO | WO 2018/213236 | A1 | 11/2018 |

OTHER PUBLICATIONS

STN Registry entry for CAS RN 2411079-49-5; Entry Date Mar. 4, 2020; Accessed via STNext Apr. 5, 2025.*

International Search Report and Written Opinion for PCT/US2021/035397, issued by the Japanese Patent Office on Sep. 7, 2021; 7 pgs.

ASTM D1200-88, "Standard Test Method for Viscosity by Ford Viscosity Cup," Dec. 1988; 3 pgs. p. 14-142.

Bassett et al., "Dual-functional, aromatic, epoxy-methacrylate monomers from bio-based feedstocks and their respective epoxy-functional thermoplastics," *J of Polymer Science*, Jan. 14, 2020; 58(5):673-682.

Fache et al., "Vanillin, a promising biobased building-block for monomer synthesis," *Green Chem*, 2014;16:1987-1998.

Hernandez, Eric, "Synthesis and Characterization of Bio-based Epoxy Resins derived from Vanillyl Alcohol," Rowan University Theses and Dissertations, Aug. 18, 2015;458. Found online https://rdw.rowan.edu/etd/458;132 pgs.

Hernandez, Eric, "Synthesis and Characterization of Bio-based Epoxy Resins derived from Vanillyl Alcohol," Supporting Information; S1-S19.

La Scala et al., Biobased Carbon Fibers and Thermosetting Resins for Use in DOD Composites Applications: SERDP WP-1758 Final Report; US Army Research Laboratory, Mar. 2017; 308 pgs.

Ramon et al., "A Review of Recent Research on Bio-Based Epoxy Systems for Engineering Applications and Potentialities in the Aviation Sector," *Aerospace*, Oct. 16, 2018;5(110): 35 pgs.

Sharma et al., "Synthesis of bis-quaternary salts of ammonia from aromatic compounds through the formation of glycidyl ether and their plant growth retardant potential," *Pesticide Research Journal*, 2008;20(2):189-193.

* cited by examiner

*Primary Examiner* — Alicia L Otton

(74) *Attorney, Agent, or Firm* — Mueting Raasch Group

(57) ABSTRACT

A method for making a monomer includes reacting an alkanol-substituted phenol with epihalohydrin in the presence of a phase transfer catalyst at a temperature of 50° C. or lower to produce a first intermediate product. The method further includes removing excess epihalohydrin, and after removing excess epihalohydrin, contacting the first intermediate product with a base to produce a second intermediate product, and forming an oxirane-functional vinyl monomer from the second intermediate product. The monomer includes an oxirane group, an unsaturated vinyl bond, and optionally an aromatic spacer between the two functional groups.

19 Claims, 3 Drawing Sheets

OXIRANE-FUNCTIONAL VINYL MONOMERS AND METHODS FOR MAKING THE SAME

CROSS-REFERENCE TO RELATED APPLICATIONS

The present application is a continuation-in-part of International Application Number PCT/US2021/035397 filed Jun. 2, 2021 which claims priority to U.S. Provisional Application No. 63/034,208, filed Jun. 3, 2020, which are incorporated herein by reference in their entireties.

FIELD

The present disclosure relates to oxirane-functional vinyl monomers and methods for making the same. The present disclosure further relates to compositions containing the oxirane-functional monomers and to polymers prepared using the oxirane-functional vinyl monomers.

BACKGROUND

Glycidyl methacrylate ("GMA") is a commonly used monomer that includes both a methacrylate moiety with an unsaturated bond and an oxirane moiety with an epoxide ring, which allow GMA to react with two kinds of polymer systems in dual curing conditions. GMA is particularly useful as a crosslinking monomer due to its dual functionality. GMA is used as a co-monomer in various industries, especially in the coatings industry. However, alternative monomers to glycidyl methacrylate are desired.

SUMMARY

The present disclosure relates to oxirane-functional vinyl monomers and methods for making the same. The oxirane-functional vinyl monomers of the present disclosure include an oxirane group, an unsaturated vinyl bond, and an aromatic spacer between the two functional groups. The present disclosure further relates to compositions containing the oxirane-functional vinyl monomers and to polymers prepared using the oxirane-functional vinyl monomers. In some embodiments, the oxirane-functional vinyl monomers are used in a coating composition, for example used to coat a food or beverage container.

According to an embodiment, a method for making a monomer includes reacting an alkanol-substituted phenol with epihalohydrin in the presence of a phase transfer catalyst at a temperature of 50° C. or lower to produce a first intermediate product. The phase transfer catalyst is preferably a quaternary ammonium salt or quaternary phosphonium salt. The method further includes removing excess epihalohydrin, and after removing excess epihalohydrin, contacting the first intermediate product with a base to produce a second intermediate product, and forming an oxirane-functional vinyl monomer from the second intermediate product.

The alkanol-substituted phenol may be a compound of Formula (I):

Formula (I)

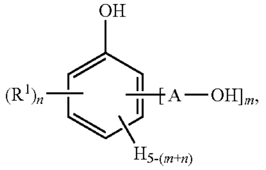

wherein A is a carbon-containing linkage group, preferably $—[C(R^2)_2]_h—$, more preferably $—C(R^2)_2—$, most preferably $—CH_2—$,

- wherein each $R^2$ is independently selected from H or a carbon-containing group, preferably H or an alkyl or alkoxy group, preferably wherein the alkyl or alkoxy group has 1 to 4 carbon atoms, more preferably wherein the alkyl or alkoxy group has a single carbon atom, most preferably wherein $R^2$ is H,
- wherein h is 1 or greater, wherein h is preferably 1 to 10, more preferably h is 1 to 6, and even more preferably h is 1 to 4, wherein each $R^1$ is independently a carbon-containing group, preferably an alkyl or alkoxy, preferably wherein $R^1$ has 1 to 4 carbon atoms, most preferably wherein $R^1$ has a single carbon atom, optionally wherein two or more of $R^1$ and/or A can join to form one or more cyclic groups (e.g., one or more aromatic rings fused to the depicted phenolic ring), wherein n is 0 to 4, preferably wherein n is 1, and wherein m is 1 to 3, preferably wherein m is 1.

The intermediate product may be a halohydrin ether of alkanol-substituted phenol according to Formula (II):

Formula (II)

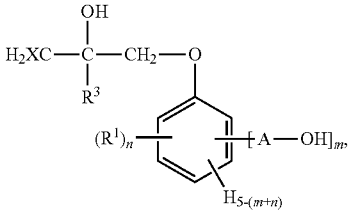

wherein A, $R^1$, m, and n are as in Formula (I), and $R^3$ is H or an alkyl, preferably wherein $R^3$ is H, and wherein X is a halogen, preferably Cl.

The oxirane-functional vinyl monomer may be a compound of Formula (III):

Formula (III)

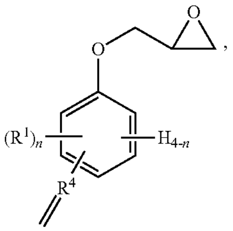

wherein $R^1$ and n are as in Formula (I), and where $R^4$ is a carbon-containing group, optionally where $R^4$ contains oxygen (e.g., as present in an ether or carboxylic linkage group of either directionality —O—C(═O)— or —C(═O)—O—), optionally where $R^4$ contains an aromatic linkage group, preferably where $R^4$ forms part of an acrylate or methacrylate group, most preferably where $R^4$ forms part of a methacrylate group.

According to an embodiment, a composition includes 80 wt-% or more of a monoglycidyl ether of an alkanol-substituted phenol, a halohydrin ether of an alkanol-substituted phenol, or a mixture thereof, measured on a non-volatile basis.

According to an embodiment, a monomer composition includes 80 wt-% or more of the compound of Formula (III), measured on a non-volatile basis.

According to an embodiment, a thermoset coating composition includes an acrylic copolymer, where the acrylic copolymer is formed from reactants (e.g., a monomer mixture) including the oxirane-functional vinyl monomer of the present disclosure.

DEFINITIONS

Figure 1A:
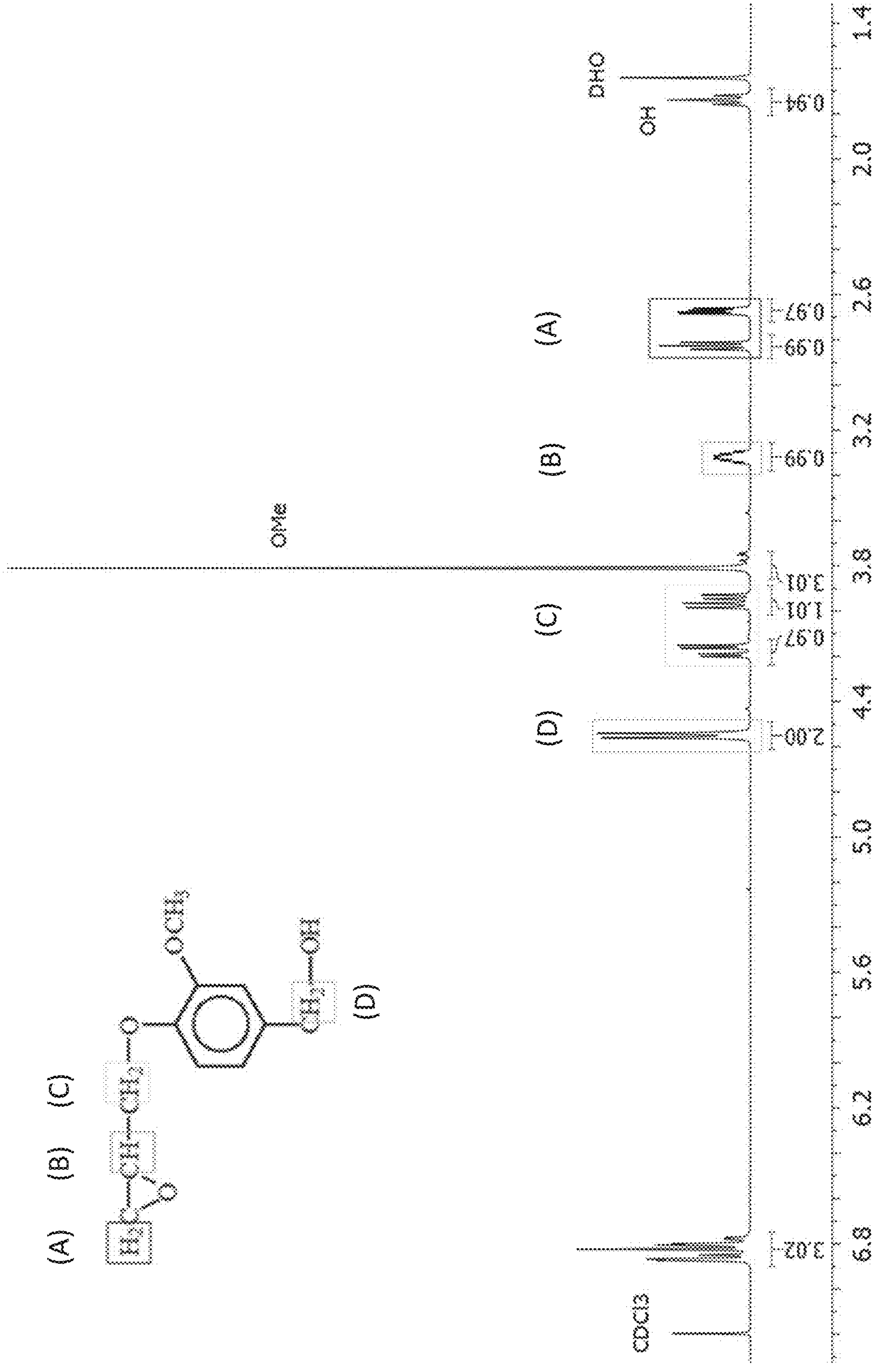
FIG. 1A is an NMR spectrum of an intermediate product in Example 1.

Unless otherwise indicated, the terms "polymer" and "polymeric material" include, but are not limited to, organic homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic, and atactic symmetries.

The term "aromatic ring" is used in this disclosure to refer to a conjugated ring system of an organic compound. Aromatic rings may include carbon atoms only, or may include one or more heteroatoms, such as oxygen, nitrogen, or sulfur.

The term "alkylated" is used in this disclosure to describe compounds that are reacted to replace a hydrogen atom or a negative charge of the compound with an alkyl group, such that the alkyl group is covalently bonded to the compound.

The term "alkyl" is used in this disclosure to describe a monovalent group that is a radical of an alkane and includes straight-chain, branched, cyclic, and bicyclic alkyl groups, and combinations thereof, including both unsubstituted and substituted alkyl groups. Unless otherwise indicated, the alkyl groups typically contain from 1 to 30 carbon atoms. In some embodiments, the alkyl groups contain 1 to 20 carbon atoms, 1 to 10 carbon atoms, 1 to 6 carbon atoms, 1 to 4 carbon atoms, or 1 to 3 carbon atoms. Examples of alkyl groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, etc.

The term "substantially" as used here has the same meaning as "significantly," and can be understood to modify the term that follows by at least about 90%, at least about 95%, or at least about 98%. The term "substantially free" of a particular compound means that the compositions of the present invention contain less than 1,000 parts per million (ppm) of the recited compound. The term "essentially free" of a particular compound means that the compositions of the present invention contain less than 100 parts per million (ppm) of the recited compound. The term "completely free" of a particular compound means that the compositions of the present invention contain less than 20 parts per billion (ppb) of the recited compound. In the context of the aforementioned phrases, the compositions of the present invention contain less than the aforementioned amount of the compound whether the compound itself is present in unreacted form or has been reacted with one or more other materials.

The term "not substantially" as used here has the same meaning as "not significantly," and can be understood to have the inverse meaning of "substantially," i.e., modifying the term that follows by not more than 25%, not more than 10%, not more than 5%, or not more than 2%.

The term "about" is used here in conjunction with numeric values to include normal variations in measurements as expected by persons skilled in the art, and is understood have the same meaning as "approximately" and to cover a typical margin of error, such as ±5% of the stated value.

Terms such as "a," "an," and "the" are not intended to refer to only a singular entity, but include the general class of which a specific example may be used for illustration.

The terms "a," "an," and "the" are used interchangeably with the term "at least one." The phrases "at least one of" and "comprises at least one of" followed by a list refers to any one of the items in the list and any combination of two or more items in the list.

As used here, the term "or" is generally employed in its usual sense including "and/or" unless the content clearly dictates otherwise. The term "and/or" means one or all of the listed elements or a combination of any two or more of the listed elements.

The recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" or "at least" a particular value, that value is included within the range.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

DETAILED DESCRIPTION

The present disclosure broadly relates to polymerizable monomers. In particular, the present disclosure relates to oxirane-functional vinyl monomers and methods for making the same. The oxirane-functional vinyl monomers of the present disclosure include an oxirane group, an ethylenically unsaturated group, and an aromatic spacer between the two functional groups. The oxirane-functional vinyl monomers may be used as crosslinking monomers. For example, the oxirane-functional vinyl monomers may be used as an alternative to glycidyl methacrylate. The present disclosure further relates to compositions containing the oxirane-functional vinyl monomers and to polymers prepared using the oxirane-functional vinyl monomers. In some embodiments, the oxirane-functional vinyl monomers are used (e.g., as structural units of a polymer) in a coating composition.

According to an embodiment, oxirane-functional vinyl monomers useful as alternatives to glycidyl methacrylate may be prepared from alkanol-substituted phenol. Such oxirane-functional vinyl monomers may be prepared by a method that has a high yield and results in a high purity end product without costly purification steps.

According to an embodiment of the present disclosure, the method includes reacting the alkanol-substituted phenol with epihalohydrin in the presence of a phase transfer catalyst at a temperature of 50° C. or lower to produce a first intermediate product. The method further includes removing excess epihalohydrin and contacting the first intermediate product with a base to produce a second intermediate product, and forming the oxirane-functional vinyl monomer from the second intermediate product.

The alkanol-substituted phenol may include any suitable substitutions that do not interfere with the reaction with epihalohydrin. In some embodiments, the alkanol-substituted phenol includes vanillyl alcohol, syringyl alcohol, salicylic alcohol, an analogue thereof, or a combination thereof. Vanillyl alcohol, syringyl alcohol, and salicylic alcohol may be obtained as products of lignin depolymerization. Other alkanol-substituted phenols may also be used. The alkanol-substituted phenols suitable for use in the methods of the present disclosure include those represented by the following Formula (I):

Formula (I)

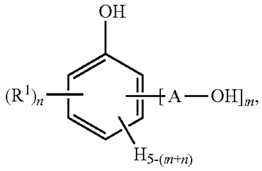

wherein A is a carbon-containing linkage group, preferably —$[C(R^2)_2]_h$—, more preferably —$C(R^2)_2$—, most preferably —$CH_2$—,

- wherein each $R^2$ is independently selected from H or a carbon-containing group, preferably H or an alkyl or alkoxy group, preferably wherein the alkyl or alkoxy group has 1 to 4 carbon atoms, more preferably wherein the alkyl or alkoxy group has a single carbon atom, most preferably wherein $R^2$ is H,
- wherein h is 1 or greater, wherein h is preferably 1 to 10, more preferably h is 1 to 6, and even more preferably h is 1 to 4, wherein each $R^1$ is independently a carbon-containing group, preferably an alkyl or alkoxy, preferably wherein $R^1$ has 1 to 4 carbon atoms, most preferably wherein $R^1$ has a single carbon atom, optionally wherein two or more of $R^1$ and/or A can join to form one or more cyclic groups (e.g., one or more aromatic rings fused to the depicted phenolic ring), wherein n is 0 to 4, preferably wherein n is 1, and wherein m is 1 to 3, preferably wherein m is 1.

Alternatively, $R^1$ may be any suitable atom or group (e.g., sulfur-containing, nitrogen-containing, phosphorus-containing, or any other group or atom having an atomic weight of 15 Dalton or more), so long as it does not unsuitably interfere with the method of forming the oxirane-functional monomer or a subsequent polymerization.

In some embodiments, the alkanol-substituted phenols may be represented by Formula (IA):

Formula (IA)

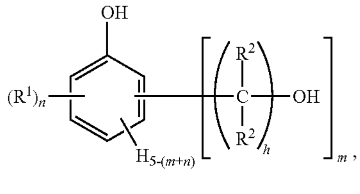

wherein each $R^1$ is independently a carbon-containing group, preferably an alkyl or alkoxy, preferably wherein $R^1$ has 1 to 4 carbon atoms, most preferably wherein $R^1$ has a single carbon atom, wherein n is 0 to 4, preferably wherein n is 1, wherein each $R^2$ is independently selected from H or a carbon-containing group, preferably H or an alkyl or alkoxy group, preferably wherein the alkyl or alkoxy group has 1 to 4 carbon atoms, more preferably wherein the alkyl or alkoxy group has a single carbon atom, most preferably wherein $R^2$ is H, wherein h is 1 or greater, wherein h is preferably 1 to 10, more preferably h is 1 to 6, and even more preferably h is 1 to 4, and wherein m is 1 to 3, preferably wherein m is 1.

In Formula (I) (or Formula (IA)), the phenolic hydroxyl group and the -$[A\text{-}OH]_m$ group may be in a para position, an ortho position, or a meta position with respect to one another. In a preferred embodiment, the phenolic hydroxyl group and the -$[A\text{-}OH]_m$ group are in a para position.

In some preferred embodiments, the alkanol-substituted phenols may be represented by Formula (TB):

Formula (IB)

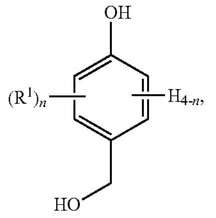

wherein each $R^1$ is independently a carbon-containing group, preferably an alkyl or alkoxy, preferably wherein $R^1$ has 1 to 4 carbon atoms, most preferably wherein $R^1$ has a single carbon atom, and wherein n is 0 to 4.

A preferred alkanol-substituted phenol is represented by Formula (IC), which is commonly known as vanillyl alcohol:

Formula (IC)

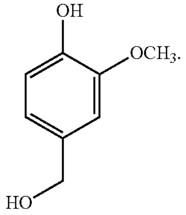

Suitable epihalohydrins that can be used in the methods of the present disclosure include those represented by the following formula:

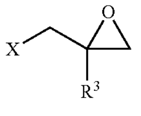

where $R^3$ is hydrogen or a hydrocarbyl group having from 1 to 4 carbon atoms, preferably hydrogen; and X is a halogen, preferably chlorine or bromine, most preferably chlorine. Epichlorohydrin is a preferred epihalohydrin for use in the methods of the present disclosure.

According to a preferred embodiment, the alkanol-substituted phenol (e.g., of Formula (I)) is reacted with epihalohydrin in the presence of a phase transfer catalyst. Examples of suitable phase transfer catalysts include various quaternary ammonium salts or quaternary phosphonium salts. Any suitable ammonium or phosphonium salt may be used. One example of a suitable ammonium salt is benzyl triethyl ammonium chloride ("TEBAC").

According to an embodiment, the alkanol-substituted phenol (e.g., of Formula (I)) is reacted with epihalohydrin in the presence of the phase transfer catalyst to form the first intermediate product at a low temperature, such as 50° C. or lower, 45° C. or lower, 40° C. or lower, or 35° C. or lower. It has been discovered that using a low temperature (e.g., 50° C. or lower) causes the epihalohydrin to react with the phenolic hydroxyl group and leaves the -[A-OH] group (e.g., methylol group) of the alkanol-substituted phenol unreacted or substantially unreacted.

Reacting the alkanol-substituted phenol (e.g., of Formula (I)) with epihalohydrin in the presence of the phase transfer catalyst at a low temperature produces a first intermediate product. According to an embodiment, the first intermediate product includes a mixture of a glycidyl-substituted intermediate and a halohydrin-substituted intermediate. According to an embodiment, the glycidyl-substituted intermediate is a monoglycidyl ether of the alkanol-substituted phenol. According to an embodiment, the halohydrin-substituted intermediate is a monohalohydrin ether of the alkanol-substituted phenol. It has been discovered that reacting the alkanol-substituted phenol (e.g., of Formula (I)) with epihalohydrin in the presence of the phase transfer catalyst (e.g., an ammonium or phosphonium salt) favors the halohydrin-substituted intermediate. Without wishing to be bound by theory, it is hypothesized that the method of the present disclosure is capable of producing oxirane-functional vinyl monomers free of or substantially free of diepoxide compounds from alkanol-substituted phenol due to the reactivity differential towards epihalohydrin between the hydroxyl group on the aromatic ring and the alkanol group (e.g., depicted -A-OH group).

The first step of the method may be characterized by the following reaction (shown without optional substitutions on the oxirane ring for simplicity):

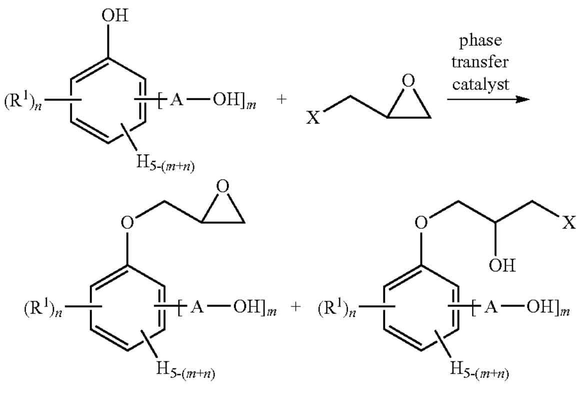

where A is a carbon-containing linkage group, preferably $-C(R^2)_2-$, most preferably $-CH_2-$, where each $R^2$ is independently selected from H, an alkyl, or a methoxy, preferably where $R^2$ is H, where each $R^1$ is independently a carbon-containing group, preferably an alkyl or alkoxy, preferably where $R^1$ has 1 to 4 carbon atoms, most preferably where $R^1$ has a single carbon atom, optionally where two or more of $R^1$ and/or A can join to form one or more cyclic groups (e.g., one or more aromatic rings fused to the depicted phenolic ring), where n is 0 to 4, preferably where n is 1, where m is 1 to 3, preferably where m is 1, and where X is a halogen, preferably Cl.

The halohydrin ether of alkanol-substituted phenol may be further represented by Formula (IIA):

Formula (IIA)

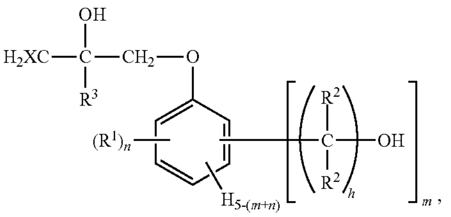

where $R^1$, $R^2$, X, m, and n are as above in the first step, and h is 1 or greater, preferably h is 1 to 10, more preferably 1 to 6, and even more preferably 1 to 4. $R^3$ is hydrogen or a hydrocarbyl group preferably having from 1 to 4 carbon atoms, preferably hydrogen.

A preferred halohydrin-substituted intermediate is the halohydrin ether of alkanol-substituted phenol represented by Formula (IIB), Formula (IIB)

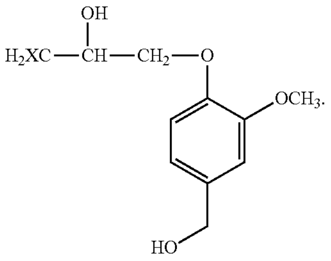

Reacting the alkanol-substituted phenol (e.g., of Formula (I)) with epihalohydrin may include combining 1 mol part of alkanol-substituted phenol with 1 mol part or more of epihalohydrin. In some embodiments, epihalohydrin is provided in excess. The method may include combining 1 mol part of alkanol-substituted phenol with 2 mol parts or more, 3 mol parts or more, 4 mol parts or more, or preferably 5 mol parts or more of epihalohydrin. The method may include combining 1 mol part of alkanol-substituted phenol with 20 mol part or less, 15 mol parts or less, 10 mol parts or less, or 8 mol parts or less of epihalohydrin. The method may include combining 1 mol part of alkanol-substituted phenol with 1 to 20 mol parts, 2 to 15 mol parts, or 3 to 10 mol parts of epihalohydrin. In one exemplary embodiment, 1 mol part of alkanol-substituted phenol is combined with about 5 mol parts of epihalohydrin.

Reacting the alkanol-substituted phenol (e.g., of Formula (I)) with epihalohydrin in the presence of the phase transfer catalyst may include combining 1 mol part of alkanol-substituted phenol with 1/1000 mol part or more, 1/100 mol part or more, 1/50 mol part or more, 1/20 mol part or more, or preferably 1/10 mol part or more of the phase transfer catalyst. The method may include combining 1 mol part of alkanol-substituted phenol with ½ mol part or less or preferably ⅕ mol parts or less of the phase transfer catalyst. As previously discussed, in preferred embodiments, the phase transfer catalyst may be a quaternary ammonium salt or a quaternary phosphonium salt, preferably a quaternary ammonium salt.

An intermediate composition containing the first intermediate product contains 80 wt-% or more, 85 wt-% or more, 90 wt-% or more, or 95 wt-% or more of a mixture of monoglycidyl ether of alkanol-substituted phenol and a halohydrin ether of alkanol-substituted phenol (the halohydrin-substituted intermediate), as measured on a non-volatile basis (that is, without solvent). The percent yield is based on the amount of monoglycidyl ether of alkanol-substituted phenol and halohydrin ether of alkanol-substituted phenol actually achieved, by weight, as compared to a theoretical maximum yield of the reaction.

If desired, one or more diluents or other materials may be present in the reaction mixture. For example, organic solvent may be included in the reaction mixture. The amount and identity of such diluents or other materials are preferably controlled to avoid unsuitable interfering with the desired reaction or with downstream reactions, including polymerization reactions, that may be used to form further products or polymers from reaction products, such as the first intermediate product.

In some embodiments, the first intermediate product may be washed. For example, the first intermediate product may be mixed with an organic solvent (such as dichloromethane or another suitable solvent) and washed with an aqueous salt solution (such as NaCl saturated water). The organic phase may further be dried, for example with anhydrous sodium sulfate. The organic phase may be filtered.

The method preferably further includes removing excess epihalohydrin and contacting the first intermediate product with a base to produce a second intermediate product. Excess epihalohydrin may be removed, for example, by distillation (such as vacuum distillation). After excess epihalohydrin is removed, less than 1 wt-% of epihalohydrin may remain in the reaction mixture.

Contacting the first intermediate product with a base converts the halohydrin ether of alkanol-substituted phenol to the glycidyl ether of alkanol-substituted phenol. According to an embodiment, contacting the first intermediate product with a base converts at least some, most, or preferably all or substantially all of the halohydrin ether of alkanol-substituted phenol to the glycidyl ether of alkanol-substituted phenol. According to a preferred embodiment, the glycidyl-substituted intermediate is a monoglycidyl ether of the alkanol-substituted phenol.

The second step of the method may be characterized by the following reaction:

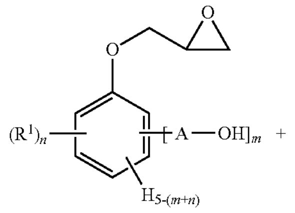

-continued

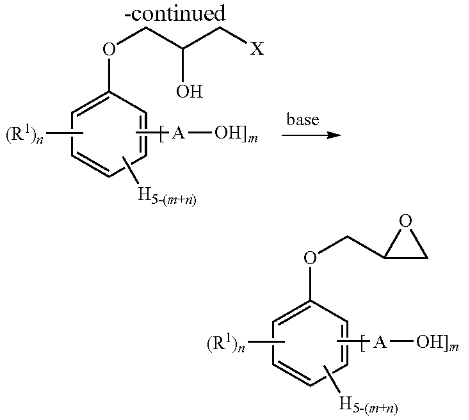

where A, $R^1$, $R^2$, X, m, and n are as above in the first step.

The method may include combining 1 mol part of the first intermediate product with at least 1 mol part of the base. In some embodiments, the base is provided in excess. The method may include combining 1 mol part of the first intermediate product with 1 mol part or more, 2 mol parts or more, 3 mol parts or more, 4 mol parts or more, or 5 mol parts or more of the base. The method may include combining 1 mol part of the first intermediate product with 10 mol parts or less, 8 mol parts or less, 5 mol parts or less, or 2 mol parts or less of the base. The base may be water soluble. The base is preferably a metallic base (e.g., a base including aluminum, calcium, lithium, magnesium, sodium, or potassium). In a preferred embodiment, the base is or includes NaOH.

The method may include contacting the first intermediate product with the base in the presence of a phase transfer catalyst to produce a second intermediate product. Examples of suitable phase transfer catalysts include various quaternary ammonium salts or quaternary phosphonium salts. Any suitable ammonium or phosphonium salt may be used. One example of a suitable ammonium salt is tetraethylammonium bromide ("TEAB").

According to an embodiment, the second intermediate product includes 70 wt-% or more, 80 wt-% or more, or 90 wt-% or more of the glycidyl-substituted intermediate (e.g., monoglycidyl ether of alkanol-substituted phenol), based on total non-volatiles in the second intermediate product.

According to an embodiment, the monoglycidyl ether of alkanol-substituted phenol has a yield of 70 wt-% or more, 80 wt-% or more, or 90 wt-% or more. The percent yield is based on the amount of monoglycidyl ether of alkanol-substituted phenol actually achieved as compared to a theoretical maximum yield of the reaction calculated based on the initial amount of alkanol-substituted phenol. In one embodiment, the monoglycidyl ether of alkanol-substituted phenol is vanillyl alcohol glycidyl ether and has a yield of 80 wt-% or more, 85 wt-% or more, or 90 wt-% or more.

The second intermediate product may also be characterized based on its epoxy equivalent weight. Epoxy equivalent weight may be determined, for example, by titration with perchloric acid. In some embodiments, the second intermediate product has an epoxy equivalent weight of 150 or greater, 175 or greater, 180 or greater, or 200 or greater, preferably 175 or greater. In some embodiments, if vanillyl alcohol is used as the alkanol-substituted phenol, the second intermediate product may have an epoxy equivalent weight of 200 or greater or 205 or greater, and up to 210 (e.g., if epichlorohydrin is used as the halohydrin).

As with the first step, if desired, one or more diluents or other materials may be present in the reaction mixture of the second step. For example, the first intermediate product may be dissolved in an organic solvent and the contacting of the first intermediate product with the base may occur in the presence of the organic solvent. The amount and identity of such diluents or other materials are preferably controlled to avoid unsuitable interference with the desired reaction or with downstream reactions, including polymerization reactions, that may be used to form further products or polymers from reaction products, such as the second intermediate product or the oxirane-functional vinyl monomer made from the second intermediate product. In one embodiment, the first intermediate product is dissolved in dichloromethane or toluene, preferably dichloromethane.

In some embodiments, the second intermediate product may be washed. For example, the second intermediate product may be washed with an aqueous salt solution (such as NaCl saturated water). The organic phase may be further dried, for example with anhydrous sodium sulfate.

The method further includes forming the oxirane-functional vinyl monomer from the second intermediate product. According to an embodiment, the oxirane-functional vinyl monomer is formed from the second intermediate product by (meth)acrylation, nucleophilic substitution with halogen functional vinyl compound, or by transesterification with an itaconic ester.

(Meth)acrylation of the second intermediate product may involve reaction with (meth)acrylic anhydride or transesterification with (meth)acrylic ester. An example of (meth) acrylation of the second intermediate product is the methacrylation of monoglycidyl ester of vanillyl alcohol with methacrylic anhydride as follows:

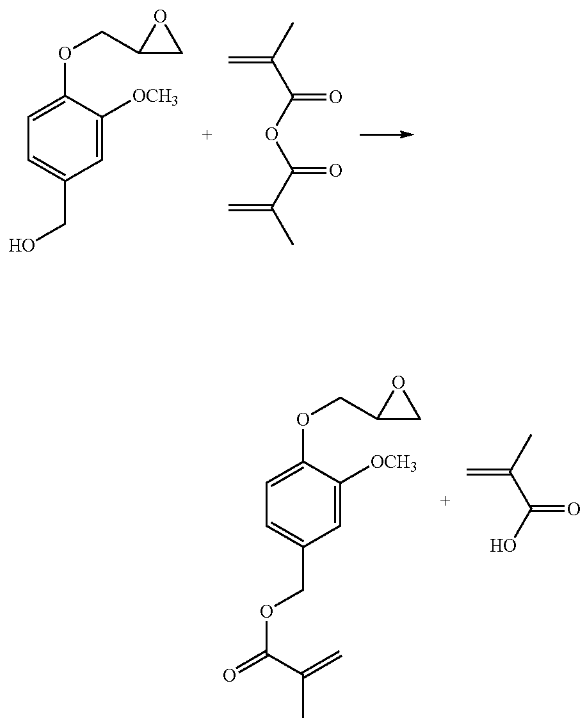

Another example of (meth)acrylation of the second intermediate product is the transesterification of monoglycidyl ester of vanillyl alcohol with methacrylic ester as follows:

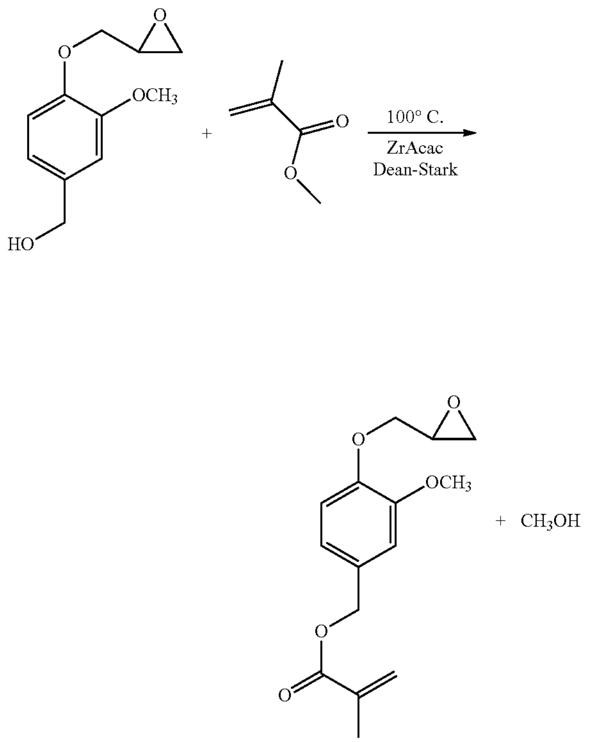

ZrAcac refers to zirconium acetyl acetonate, used as a transesterification catalyst.

Nucleophilic substitution with a halogenated compound bearing a double bond is known as the Williamson Synthesis. Examples of nucleophilic substitution onto the glycidyl-substituted intermediate include substitution onto monoglycidyl ester of vanillyl alcohol using (A) α-chloromethyl styrene (also known as 4-vinylbenzyl chloride) or (B) 2-chloroethyl vinyl ether as follows:

(A)

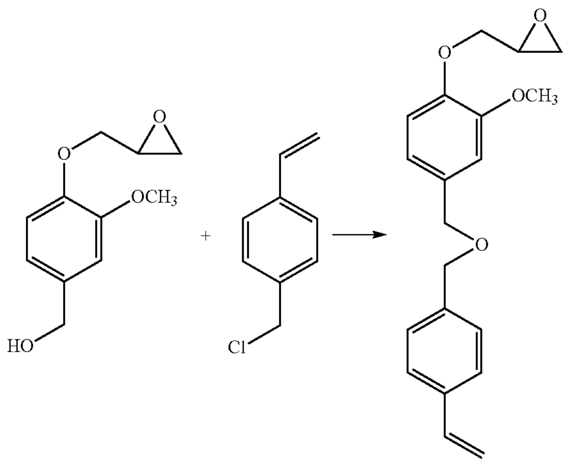

-continued (B)

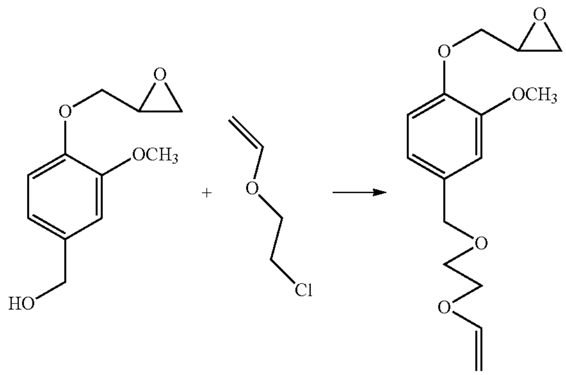

Transesterification of the glycidyl-substituted intermediate with an itaconic ester may produce a mixture of mono-vinyl-functional monoglycidyl ether and diglycidyl ether. An example of the transesterification with itaconic ester is the transesterification reaction of monoglycidyl ether of vanillyl alcohol with diethyl itaconate as follows:

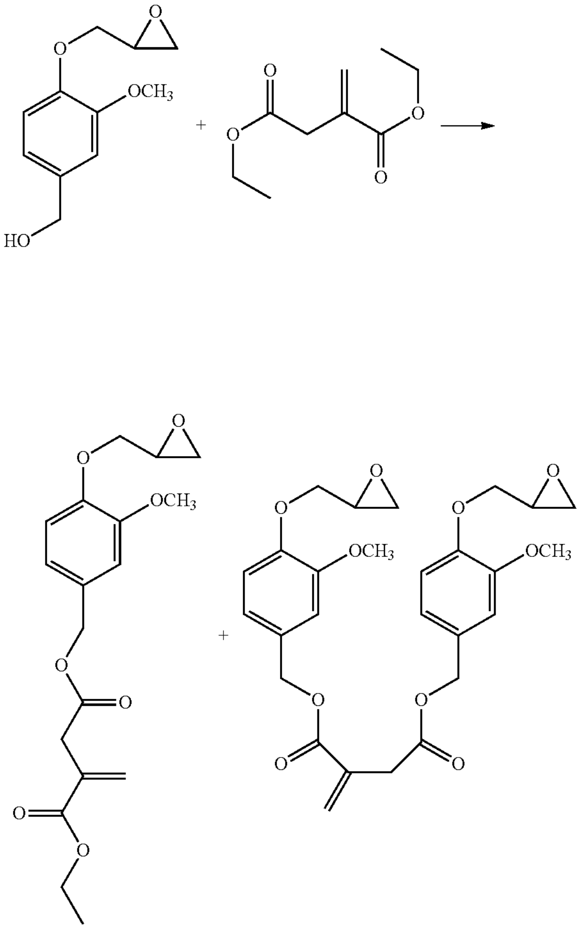 [SMILES: COc1cc(CO)ccc1OCC1CO1 ; C=C(CC(=O)OCC)C(=O)OCC ; C=C(CC(=O)OCc1ccc(OCC2CO2)c(OC)c1)C(=O)OCC ; C=C(CC(=O)OCc1ccc(OCC2CO2)c(OC)c1)C(=O)OCc1ccc(OCC2CO2)c(OC)c1]

According to an embodiment, the oxirane-functional vinyl monomer includes an oxirane moiety and a vinyl moiety. In some embodiments, the vinyl moiety is part of a (meth)acrylate moiety. The oxirane-functional vinyl monomer may be represented by Formula (III) as follows:

Formula (III)

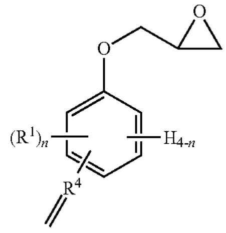

where each $R^1$ is independently a carbon-containing group, preferably an alkyl or alkoxy, preferably where $R^1$ has 1 to 4 carbon atoms, most preferably where $R^1$ has a single carbon atom, where n is 0 to 4, preferably where n is 1, where $R^4$ is a carbon-containing group, optionally where $R^4$ contains oxygen (e.g., as present in an ether or carboxylic linkage group of either directionality —O—C(═O)— or —C(═O)—O—), optionally where $R^4$ contains an aromatic linkage group, preferably where $R^4$ forms part of an acrylate or methacrylate group, most preferably where $R^4$ forms part of a methacrylate group. $R^4$ may include one or more pendent groups, which may be located at any suitable location, including, for example, at the carbon atom of the depicted carbon double bond.

In some embodiments, the oxirane-functional vinyl monomer may be represented by Formula (IIIA) as follows:

Formula (IIIA)

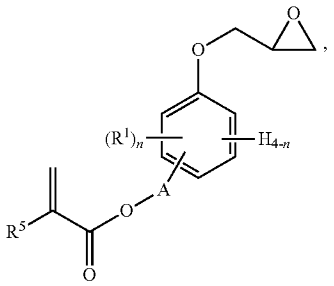

wherein A, $R^1$, m, and n are as in Formula (I), and wherein $R^5$ is H or a carbon-containing group, preferably wherein $R^5$ is H or alkyl, most preferably wherein $R^5$ is H or methyl.

In some embodiments, the oxirane-functional vinyl monomer may be represented by Formula (IIIB) as follows:

Formula (IIIB)

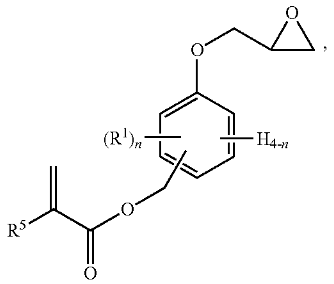

where $R^1$, $R^5$, and n are as in Formula (IIIA) above.

In some embodiments, the oxirane-functional vinyl monomer may be represented by Formula (IIIC) as follows:

Formula (IIIC)

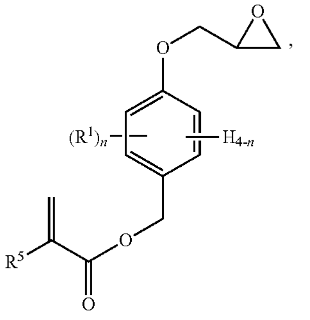

where $R^1$, $R^5$, and n are as in Formula (IIIA) above.

In some embodiments, the oxirane-functional vinyl monomer is vanillyl alcohol epoxy-methacrylate (VAEM), represented by Formula (IIID) as follows:

Formula (IIID)

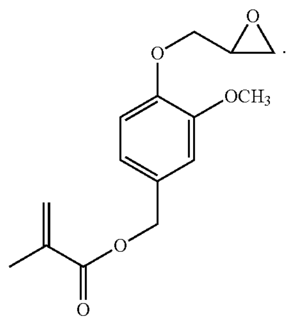

In some embodiments, a monomer composition contains 75 wt-% or more, 80 wt-% or more, 85 wt-% or more, 90 wt-% or more, or 95 wt-% or more of the compound of Formula (III), Formula (IIIA), Formula (TIM), Formula (IIIC), or Formula (IIID). The purity of the composition may be determined using any suitable analytical technique. An example of a useful quantitative technique is gas chromatography (GC) combined with a suitable detection method, such as mass spectrometry (MS). GC-MS may be complemented with liquid chromatography (LC) and an ultraviolet-visible light detector (UV-Vis) if impurities or other components are difficult to detect using GC-MS. Preferably the level of purity of the monomer composition is achieved without chromatographic separation steps. In other words, according to an embodiment, the method does not include a chromatographic separation step. However, the method may include various washing, drying, extraction, and/or filtration steps. For example, the method may include washing the first intermediate product, the second intermediate product, the oxirane-functional vinyl monomer, or a combination thereof. According to an embodiment, less than 1000 ppm, less than 500 ppm, less than 100 ppm, less than 50 ppm, less than 25 ppm, or less than 10 ppm of epihalohydrin remains in the reaction mixture after forming of the oxirane-functional vinyl monomer. The unit "ppm" (parts per million) is used here to refer to the amount by weight.

In some embodiments, the oxirane-functional vinyl monomer is used in a coating composition. For example, the oxirane-functional vinyl monomer may be used in a thermoset coating composition. In an embodiment, the thermoset coating composition contains an acrylic copolymer, where the acrylic copolymer includes the oxirane-functional vinyl monomer (e.g., includes one or more structural units derived from the oxirane-functional vinyl monomer). In one embodiment, the acrylic copolymer includes an emulsion polymerized latex polymer. In one embodiment, the emulsion polymerized latex polymer is formed by emulsion polymerizing an ethylenically unsaturated monomer mixture including an oxirane-functional vinyl monomer of any preceding embodiment in the presence of a salt of an acid- or anhydride-functional polymer (e.g., a salt of an acid- or anhydride-functional organic solution polymerized acrylic copolymer), polyester polymer (e.g., a salt of an acid or anhydride-functional polyester-acrylic copolymer), or polyether polymer (e.g., a salt of an acid or anhydride-functional polyether-acrylic copolymer).

The emulsion polymerized latex polymers may be prepared using any suitable materials and processes. For example, one or more ethylenically unsaturated monomer components may be emulsion polymerized in aqueous media with the assistance of one or more emulsifiers, which may be a polymeric surfactant (e.g., salt of a base and acid- or anhydride-functional polymer), a non-polymeric surfactant (e.g., an anionic surfactant, cationic surfactant, zwitterionic surfactant, nonionic surfactant, or a combination thereof), or a mixture thereof. The surfactant can be any suitable type of surfactant and may, for example, be a "lower" molecular-weight surfactant (e.g., a surfactant that is non-polymeric or has a number average molecular weight of less than about 1,000 Daltons, more typically less than about 750 Daltons, and even more typically less than about 500 Daltons). Examples of suitable anionic surfactants include dodecylbenzene sulfonic acid, dinonylnaphthalene sulfonic acid, dinonylnaphthylenedisulfonic acid, bis(2-ethylhexyl)sulfosuccinic acid, dioctyl sulfosuccinic acid, sodium lauryl sulfate, sodium dodecyl sulfate, sodium laureth sulfate, fatty acid (ester) sulfonate, polyaryl ether phosphate acid or sulfonate acid, and the like, including mixtures thereof. In certain embodiments, a polymeric surfactant is used which has, for example, a number average molecular weight greater than about 2,000 Daltons or even greater than about 4,000 Daltons. In some embodiments, a polymerizable surfactant is used. Examples of suitable polymerizable surfactants include those disclosed in U.S. Patent Application Publication No. US 2002/0155235 A1; and those commercially available as REASOAP™ from Adeka Corporation in Tokyo, Japan; NOIGEN™ and 30 HITENOL™ from Da-Ichi Kogyo Siyyaku Co., Ltd. in Tokyo, Japan; and SIPOMER™ from Solvay Rhodia in Brussels, Belgium. Examples of suitable non-ionic surfactants include ethoxylated compounds. In some embodiments, the non-ionic compound is a sucrose ester, sorbitan ester, alkyl glycoside, glycerol ester, or mixture thereof. In some embodiments, a non-ionic surfactant is used that includes hydroxyl groups. Non-ionic surfactants that comprise, or are derived from, polysorbate compounds may be used in some embodiments. In some embodiments, a surfactant or mixture of surfactants as described in International Application Publication No. WO 2017/112837 A1 entitled "Latex Polymer Made Using Metallic-Base-Neutralized Surfactant and Blush-Resistant Coating Compositions Containing Such Polymers" may be used. In one embodiment, the acrylic copolymer includes an organic solution polymerized polymer.

In one embodiment, the acrylic copolymer has a calculated Tg (e.g., Fox equation Tg) of 0° C. or more, 20° C. or more, 40° C. or more, 50° C. or more, 60° C. or more, or 70° C. or more.

In some embodiments, the coating composition includes 5 wt-% or more, 10 wt-% or more, 20 wt-% or more, 35 wt-% or more, 50 wt-% or more, 65 wt-% or more, 80 wt-% or more, 90 wt-% or more, or 95 wt-% or more, or even 99 wt-% or more of the acrylic copolymer, based on total resin solids included in the coating composition. In some embodiments, the coating composition includes 100 wt-% or less, 95 wt-% or less, 90 wt-% or less, 80 wt-% or less, 60 wt-% or less, 40 wt-% or less, 20 wt-% or less, 10 wt-% or less of the acrylic copolymer, based on total resin solids included in the coating composition.

In some embodiments, the oxirane-functional vinyl monomer constitutes 1 wt-% or more, 2 wt-% or more, 5 wt-% or more, or 10 wt-% or more of the ethylenically unsaturated monomers used to make the acrylic copolymer. The oxirane-functional vinyl monomer may constitute 90 wt-% or less, 75 wt-% or less, 50 wt-% or less, 30 wt-% or less, 20 wt-% or less, or 10 wt-% or less of the ethylenically unsaturated monomers used to make the acrylic copolymer. In some embodiments, the oxirane-functional vinyl monomer constitutes 1 wt-% to 20 wt-%, or 5 wt-% to 10 wt-% of the acrylic copolymer. In one embodiment, the acrylic copolymer comprises a reaction product of a tertiary amine, an oxirane-functional acrylic copolymer, and an acid-functional polymer.

In some embodiments the oxirane-functional vinyl monomer or an acrylic copolymer made with the oxirane-functional vinyl monomer may be included in a coating composition in an amount consistent with being used as a formulation additive (e.g., as an adhesion promoter). In other embodiments, the oxirane-functional vinyl monomer or an acrylic copolymer made with the oxirane-functional vinyl monomer may be included in a substantial or predominant amount of a coating composition, such as a film-forming resin system of the coating composition.

In some embodiments, the oxirane-functional vinyl monomer is used in a coating composition used to coat a surface of a food or beverage container. Packaging coatings preferably are capable of high-speed application to the substrate of the packaging (typically a surface of a metal substrate of a food or beverage can or other type of container, or a portion thereof), and provide the desired properties when hardened. For example, a preferred coating is safe for food contact, has excellent adhesion to the substrate, has sufficient flexibility to withstand deflection of the underlying substrate without rupturing (e.g., during fabrication steps or damage occurring during transport or use of the packaging article), and resists degradation over long periods of time, even when exposed to harsh environments. According to an embodiment, the oxirane-functional vinyl monomer of the present disclosure is suitable for use in a coating (interior or exterior coating) applied to a food or beverage container, or a portion thereof, prior to or after formation of the food or beverage container or portion thereof. In some embodiments, the coating composition is a solvent-based or aqueous food or beverage can coating composition. The food or beverage container or a portion thereof may have a metal substrate and a coating disposed on an interior or exterior surface of at least a portion of the metal substrate formed of the thermoset coating composition.

The oxirane-functional vinyl monomers of the present disclosure may form part of a polymerizable composition. The oxirane-functional vinyl monomers may form part of a monomer composition, a co-polymer composition, a polymer composition, a latex dispersion, or a polymeric coating. The oxirane-functional vinyl monomers may be used as a cross-linker and/or as part of a copolymer composition.

The coating composition may include various additional components, such as crosslinking agents and other additives.

The choice of a particular crosslinking agent (sometimes referred to as a "crosslinking resin" or "crosslinker"), if used, typically will depend on the particular product being formulated. For example, some coatings are highly colored (e.g., gold-colored coatings). These coatings may typically be formulated using crosslinkers that themselves tend to have a yellowish color. In contrast, white coatings are generally formulated using non-yellowing crosslinkers, or only a small amount of a yellowing crosslinker. Preferred crosslinking agents are substantially free of BPA, BPF, BPS, glycidyl ether compounds thereof (e.g., BADGE), and epoxy novolacs. Any of a variety of hydroxyl-reactive or carboxyl-reactive crosslinking agents may be used, including phenoplast, aminoplast and blocked or non-blocked isocyanate crosslinking agents, beta-hydroxy alkylamides, as well as combinations thereof. Exemplary phenoplast resins include the condensation products of aldehydes with phenols, with formaldehyde and acetaldehyde being preferred aldehydes. Exemplary phenols include phenol, cresol, p-phenylphenol, p-tert-butylphenol, p-tert-amylphenol, and cyclopentylphenol. Exemplary aminoplast resins include the condensation products of aldehydes such as formaldehyde, acetaldehyde, crotonaldehyde, and benzaldehyde with amino or amido group containing substances such as urea, melamine, and benzoguanamine. Examples of suitable aminoplast crosslinking resins include benzoguanamine-formaldehyde resins, melamineformaldehyde resins, esterified melamine-formaldehyde, and urea-formaldehyde resins. One specific example of a suitable aminoplast crosslinker is the fully alkylated melamineformaldehyde resin commercially available from Cytec Industries, Inc. under the trade name of CYMEL 303. Exemplary blocked or non-blocked isocyanates include aliphatic, cycloaliphatic or aromatic di-, tri-, or poly-valent isocyanates, such as hexamethylene diisocyanate (HMDI), cyclohexyl-1,4-diisocyanate, and the like. Further examples of generally suitable blocked isocyanates include isomers of isophorone diisocyanate, dicyclohexylmethane diisocyanate, toluene diisocyanate, diphenylmethane diisocyanate, phenylene diisocyanate, tetramethyl xylene diisocyanate, xylylene diisocyanate, and mixtures thereof. In some embodiments, blocked isocyanates are used that have a number-average molecular weight of at least about 300, more preferably at least about 650, and even more preferably at least about 1,000.

The concentration of crosslinking agent in the coating composition may depend on the type of crosslinking agent, the time and temperature of the bake, and the molecular weights of the copolymer particles. When used, the crosslinker is typically present in an amount of up to about 50% by weight, preferably up to about 30% by weight, and more preferably up to about 15% by weight. When used, the crosslinker is typically present in an amount of at least about 0.1% by weight, more preferably at least about 1% by weight, and even more preferably at least about 1.5% by weight. These weight percentages are based on the total resin solids weight of the coating composition.

In some embodiments, the coating composition is substantially free of formaldehyde and formaldehyde-containing materials, more preferably essentially free of these compounds, even more preferably essentially completely free of these compounds, and most preferably completely free of these compounds.

The coating composition may optionally include one or more additives. When used, the additives preferably enhance and preferably do not adversely affect the latex emulsion, or a cured coating formed from the coating composition. For example, additives may be included in the coating composition to enhance composition aesthetics, to facilitate manufacturing, processing, handling, and application of the composition, and to further improve a particular functional property of the coating composition or a cured coating resulting therefrom. Such optional additives include, for example, catalysts, dyes, pigments, toners, extenders, fillers, lubricants, anticorrosion agents, flow control agents, thixotropic agents, dispersing agents, antioxidants, adhesion promoters, light stabilizers, co-resins and mixtures thereof. Each optional additive is preferably included in a sufficient amount to serve its intended purpose, but not in such an amount to adversely affect the coating composition or a cured coating resulting therefrom.

One preferred optional additive is a catalyst to increase the rate of cure. Examples of catalysts, include, but are not limited to, strong acids (e.g., dodecylbenzene sulfonic acid (DDBSA, available as CYCAT 600 from Cytec), methane sulfonic acid (MSA), p-toluene sulfonic acid (pTSA), dinonylnaphthalene disulfonic acid (DNNDSA), and triflic acid), quaternary ammonium compounds, phosphorous compounds, and tin, titanium, and zinc compounds. Specific examples include, but are not limited to, a tetraalkyl ammonium halide, a tetraalkyl or tetraaryl phosphonium iodide or acetate, tin octoate, zinc octoate, triphenylphosphine, and similar catalysts known to persons skilled in the art.

If used, the catalyst is preferably present in an amount of at least about 0.01% by weight, and more preferably at least about 0.1% by weight, based on the total solids weight of the coating composition. Furthermore, if used, the catalyst is also preferably present in an nonvolatile amount of no greater than about 3% by weight, and more preferably no greater than about 1% by weight, based on the total solids weight of the coating composition.

Another useful optional additive is a lubricant (e.g., a wax), which facilitates manufacture of metal closures and other fabricated coated articles by imparting lubricity to sheets of coated metal substrate. Preferred lubricants include, for example, Carnauba wax and polyethylene-type lubricants. If used, a lubricant is preferably present in the coating composition in an amount of at least about 0.1% by weight, and preferably no greater than about 2% by weight, and more preferably no greater than about 1% by weight, based on the total solids weight of the coating composition.

Another useful optional additive is an organosilicon material, such as siloxane-based or polysilicon-based materials. Representative examples of suitable such materials are disclosed in International Application Nos. WO 2014/089410 A1 and WO 2014/186285 A1.

Another useful optional ingredient is a pigment, such as titanium dioxide. If used, a pigment is present in the coating composition in an amount of no greater than about 70% by weight, more preferably no greater than about 50% by weight, and even more preferably no greater than about 40% by weight, based on the total solids weight of the coating composition.

In preferred embodiments, the coating composition is substantially free or completely free of any structural units derived from bisphenol A ("BPA"), bisphenol F ("BPF"), bisphenol S ("BPS"), or any diepoxides thereof (e.g., diglycidyl ethers thereof such as the diglycidyl ether of BPA ("BADGE")). In addition, the coating composition is preferably substantially free or completely free of any structural units derived from a dihydric phenol, or other polyhydric phenol, having estrogenic agonist activity great than or equal to that of 4,4'-(propane-2,2-diyl)diphenol. More preferably, the coating composition is substantially free or completely free of any structural units derived from a dihydric phenol, or other polyhydric phenol, having estrogenic agonist activity greater than or equal to that of BPS. In some embodiments, the coating composition is substantially free or completely free of any structural units derived from a bisphenol.

Even more preferably, the coating composition is substantially free or completely free of any structural units derived from a dihydric phenol, or other polyhydric phenol, having estrogenic agonist activity greater than 4,4'-(propane-2,2-diyl)bis(2,6-dibromophenol). Optimally, the coating composition is substantially free or completely free of any structural units derived from a dihydric phenol, or other polyhydric phenol, having estrogenic agonist activity greater than 2,2-bis(4-hydroxyphenyl)propanoic acid. The same is preferably true for any other components of a composition including the coating composition. See, for example, U.S. Application Publication No. US 2013/0316109 A1, incorporated herein by reference in its entirety, for a discussion of such structural units and applicable test methods.

In some further embodiments, the coating composition is substantially free or completely free of any acrylamide-type monomers (e.g., acrylamides or methacrylamide). Moreover, in some embodiments, the coating composition is substantially free or completely free of one or more of styrene (whether free or polymerized) or substituted styrene compounds (whether free or polymerized). As discussed above, in these embodiments, the reactant monomers may include other ethylenically-unsaturated aromatic compounds or ethylenically unsaturated alicyclic compounds, such as aromatic (meth)acrylates or alicyclic (meth)acrylates, for example. In additional further embodiments, the coating composition is substantially free or completely free of halogenated monomers (whether free or polymerized), such as chlorinated vinyl monomers.

The coating composition may also optionally be rheologically modified for different coating applications. For example, the coating composition may be diluted with additional amounts of the aqueous carrier to reduce the total solids content in the coating composition. Alternatively, portions of the aqueous carrier may be removed (e.g., evaporated) to increase the total solids content in the coating composition. The final total solids content in the coating composition may vary depending on the particular coating application used (e.g., spray coating), the particular coating use (e.g., for interior can surfaces), the coating thickness, and the like.

In some embodiments, the coating composition preferably has a total solids weight greater than about 5%, more preferably greater than about 10%, and even more preferably greater than about 15%, based on the total weight of the coating composition. In liquid embodiments, the coating composition also preferably has a total solids weight less than about 80%, more preferably less than about 60%, and even more preferably less than about 50%, based on the total weight of the coating composition. The liquid carrier (e.g., aqueous or organic solvent carrier) may constitute the remainder of the weight of the coating composition.

In some embodiments, such as for certain spray coating applications (e.g., inside spray for food or beverage cans including, e.g., aluminum beverage cans), the coating composition may have a total solids weight greater than about 5%, more preferably greater than about 10%, and even more preferably greater than about 15%, based on the total weight of the coating composition. In these embodiments, the coating composition may also have a total solids weight less than about 40%, more preferably less than about 30%, and even more preferably less than about 25%, based on the total weight of the coating composition. In some of these embodiments, the coating composition may have a total solids weight ranging from about 18% to about 22%. The aqueous carrier may constitute the remainder of the weight of the coating composition.

If desired, the coating composition may also include one or more other optional polymers in addition to the acrylic copolymers, such as, for example, one or more acrylic polymers, alkyd polymers, epoxy polymers, polyolefin polymers, polyurethane polymers, polysilicone polymers, polyester polymers, and copolymers and mixtures thereof.

As previously discussed, the aqueous carrier of the coating composition preferably includes water and may further include one or more optional organic solvents. In some embodiments, water constitutes greater than about 20% by weight, more preferably greater than about 35% by weight, and even more preferably greater than about 50% by weight of the total weight of the aqueous carrier. In some embodiments, water constitutes 100% or less, more preferably less than about 95% by weight, and even more preferably less than about 90% by weight of the total weight of the aqueous carrier.

While not intending to be bound by theory, the inclusion of a suitable amount of an organic solvent can be advantageous in some embodiments (e.g., for certain coil coating applications to modify flow and leveling of the coating composition, control blistering, and maximize the line speed of the coil coater). Accordingly, in certain embodiments, the organic solvents may constitute greater than 0%, more preferably greater than about 5%, and even more preferably greater than about 10% by weight of the aqueous carrier, based on the total weight of the aqueous carrier. In these embodiments, the organic solvents may also constitute less than about 80%, more preferably less than about 50%, and even more preferably less than about 40% by weight of the aqueous carrier, based on the total weight of the aqueous carrier.

The coating composition preferably has a viscosity suitable for a given coating application. In some embodiments, such as for certain spray coating applications, the coating composition may have an average viscosity greater than about 5 seconds, more preferably greater than 10 seconds, and even more preferably greater than about 15 seconds, based on the Viscosity Test described below (Ford Viscosity Cup #4 at 25° C.). In some embodiments, the coating composition may also have an average viscosity less than about 40 seconds, more preferably less than 30 seconds, and even more preferably less than about 25, based on the Viscosity Test described below.

The coating composition of the present disclosure with the aqueous dispersion of the latex copolymer particles may be applied on a variety of different substrates using a variety of different coating techniques. In preferred embodiments, the coating composition is applied as an inside spray coating. As briefly described above, cured coatings formed from the coating composition are particularly suitable for use on metal food and beverage cans (e.g., two-piece cans, three-piece cans, and the like). Two-piece cans (e.g., two-piece beer or soda cans and certain food cans) are typically manufactured by a drawn and ironing ("D&I") process. The cured coatings are also suitable for use in food or beverage contact situations (collectively referred to herein as "food-contact"), and may be used on the inside or outside of such cans.

Preferred inside spray coating compositions of the present disclosure are capable of being spray applied on an interior of a food or beverage can (e.g., a 2-piece food or beverage can) to effectively, and evenly, coat the substrate and form a continuous cured coating (e.g., a coating that exhibits a suitable initial metal exposure value, thereby indicating that the substrate has been effectively coated and is free of unsuitable holes or other discontinuities in the coating).

Suitable curing temperatures for the coating composition of the present disclosure are greater than about 150° C. (about 300° F.), more preferably greater than about 165° C. (about 330° F.), and even more preferably greater than about 180° C. (about 360° F.). In some embodiments, suitable curing temperatures for the coating composition of the present disclosure are also less than about 220° C. (about 430° F.), more preferably less than about 205° C. (about 400° F.), and even more preferably less than about 195° C. (about 380° F.). Suitable residence times for the above-discussed temperatures range from about 40 seconds to about three minutes, more preferably about one minute to about two minutes. After curing, the resulting cured coatings (e.g., coating 34) may have suitable film thicknesses for protecting the cans from food or beverage products that are subsequently filled into the cans.

The desired film thickness for the cured coating may vary depending on the particular food or beverage to be filled in a given can. In some embodiments for the spray coating application (e.g., inside spray for food or beverage cans), the average film thickness after curing is greater than about 0.7 milligrams/square-inch (mg/inch$^2$), more preferably greater than about 0.8 mg/inch2, and even more preferably greater than about 0.9 mg/inch$^2$. In these embodiments, the average film thickness after curing is also less than about 4.0 mg/inch$^2$, more preferably less than about 3.0 mg/inch2, and even more preferably less than about 2.5 mg/inch$^2$.

In some further embodiments, the average film thickness after curing ranges from about 0.9 mg/inch$^2$ to about 1.1 mg/inch$^2$. In other further embodiments, the average film thickness after curing ranges from about 1.4 mg/inch$^2$ to about 1.6 mg/inch$^2$. In yet other further embodiments, the average film thickness after curing ranges from about 1.9 mg/inch$^2$ to about 2.1 mg/inch$^2$.

Alternatively, the coating composition may optionally be applied as a coil coating. During a coil coating application, a continuous coil composed of a metal (e.g., steel or aluminum) is coated with the coating composition of the present disclosure. Once coated, the coating coil may be subjected to a short thermal, ultraviolet, or electromagnetic curing cycle, for hardening (e.g., drying and curing) of the coating composition. Coil coatings provide coated metal (e.g., steel or aluminum) substrates that can be fabricated into formed articles, such as two-piece drawn food cans, food can ends, drawn and ironed cans, beverage can ends, and the like.

The coating composition of the present disclosure also offers utility in other coating applications. These additional applications include, but are not limited to, wash coating, sheet coating, and side seam coatings (e.g., food can side seam coatings). Other commercial coating application and curing methods are also envisioned, for example, electrocoating, extrusion coating, laminating, powder coating, and the like. The coating composition may also be useful in medical or cosmetic packaging applications, including, for example, on surfaces of metered dose inhalers ("MDIs"), including on drug-contact surfaces.

In some embodiments, the coating composition of the present disclosure may be a powder coating composition prepared and/or applied using any suitably techniques, including, for example, any of the techniques described in U.S. Pat. Publ. No. 2021/0147692. For example, the powder polymer particles may be prepared using an emulsion, suspension, solution, or dispersion polymerization method, which are well-known to those skilled in the art. In some embodiments, a polymer may be prepared (e.g., using a monomer mixture of the present disclosure) in the form of an aqueous emulsion, suspension, solution, or dispersion using standard techniques and subsequently dried to form particles using any of a variety of techniques including, for example, spray drying, fluidized bed drying, vacuum drying, radiant drying, freeze drying, and flash drying, among others. Preferably, drying involves spray drying. For example, a polymer may be prepared in the form of an aqueous emulsion/dispersion/suspension/solution technique and subsequently dried using, for example, a spray drying technique. Spray drying may form agglomerates directly. Spray drying involves the atomization of a liquid feedstock into a spray of droplets and contacting the droplets with hot air in a drying chamber. The sprays are typically produced by either rotary (wheel) or nozzle atomizers. Evaporation of moisture from the droplets and formation of dry particles proceed under controlled temperature and airflow conditions. Powder particles are typically discharged substantially continuously from the drying chamber. Operating conditions and dryer design are selected according to the drying characteristics of the product specification.

During the above-discussed curing steps, the aqueous carrier is preferably vaporized or otherwise dried off from the latex copolymer, allowing the copolymer molecules to cure. If desired, the drying and curing steps may be combined in a single step or carried out in separate steps.

Preferred glass transition temperatures for the cured coating of the present disclosure (and particularly interior, food-contact coatings) include those greater than about 50° C., more preferably greater than about 60° C., even more preferably greater than about 70° C., and in some embodiments, greater than about 80° C. Preferred glass transition temperatures for the cured coating include those less than about 120° C., more preferably less than about 115° C., even more preferably less than about 110° C., and in some embodiments, less than about 100° C. The glass transition temperatures can be measured by dynamic mechanical analysis (DMA) or differential scanning calorimetry (DSC). Some multi-unsaturated monomers typically gel when forming homopolymers, which can limit the effectiveness of theoretical calculations using the Flory-Fox Equation.

To further prevent or otherwise reduce coating penetration by an intended food or beverage product, the cured coating is preferably suitably hydrophobic. For example, the cured coating can have a contact angle with deionized water greater than about 90, more preferably greater than about 95, and even more preferably greater than about 100.

The cured coating preferably exhibits desired properties for use as an inside spray coating for food and beverage containers. For example, the cured coating preferably gives a global extraction of less than about 25 parts-per-million (ppm), and more preferably less than about 10 ppm, and even more preferably less than about 1 ppm, pursuant to the Global Extraction test below. Additionally, the cured coating preferably exhibits a metal exposure less than about 5 milliamps (mA), more preferably less than about 2 mA, and even more preferably less than about 1 mA, pursuant to the Initial Metal Exposure test below.

Flexibility is also important so that the coating can deflect with the metal substrate during post-cure fabrication steps (necking and dome reformation) and if the can is dropped from a reasonable height during transport or use. In some preferred embodiments, the cured coating should preferably exhibit a metal exposure less than about 3.5 mA, more preferably less than about 2.5 mA, and even more preferably less than about 1.5 mA, pursuant to the Metal Exposure After Drop Damage test below.

Moreover, the coating composition (uncured) should preferably exhibit substantially no change (e.g., a change in viscosity, if any, of less than 25%, more preferably less than 10%, even more preferably less than 5%, and even more preferably less than 1%) in viscosity pursuant to the Pot Life Stability test below. Accordingly, the coating composition of the present disclosure is particularly suitable for use as an inside spray coating composition for containers configured to retain a variety of different food or beverage products.

Viscosity Test. This test measures the viscosity of a latex emulsion or coating composition for rheological purposes, such as for sprayability and other coating application properties. The test is performed pursuant to ASTM D1200-88 using a Ford Viscosity Cup #4 at 25° C. The results are measured in the units of seconds.

Global Extraction Test. The global extraction test is designed to estimate the total amount of mobile material that can potentially migrate out of a coating and into food packed in a coated can. Typically coated substrate is subjected to water or solvent blends under a variety of conditions to simulate a given end use. Acceptable extraction conditions and media can be found in 21 CFR § 175.300 paragraphs (d) and (e). The allowable global extraction limit as defined by the FDA regulation is 50 parts per million (ppm).

The extraction procedure that can be used in the current invention is described in 21 CFR § 175.300 paragraph (e)(4)(xv) with the following modifications to ensure worst-case scenario performance: (1) the alcohol (ethanol) content is increased to 10% by weight, and (2) the filled containers are held for a 10-day equilibrium period at 37.8° C. (100° F.). These conditions are per the FDA publication "Guidelines for Industry" for preparation of Food Contact Notifications.

The coated beverage can is filled with 10% by weight aqueous ethanol and subjected to pasteurization conditions (65.6° C., 150° F.) for 2 hours, followed by a 10-day equilibrium period at 37.8° C. (100° F.). Determination of the amount of extractives is determined as described in 21 CFR § 175.300 paragraph (e) (5), and ppm values are calculated based on surface area of the can (no end) of 44 square inches with a volume of 355 milliliters. Preferred coatings should give global extraction results of less than 50 ppm, more preferred results of less than 10 ppm, even more preferred results of less than 1 ppm. Most preferably, the global extraction results are optimally non-detectable.

Initial Metal Exposure Test. This test method determines the amount of the inside surface of the can that has not been effectively coated by the sprayed coating. This determination is made through the use of an electrically conductive solution (1% NaCl in deionized water). The interior "inside spray" coating is typically applied using a high pressure airless spray. The following film weights are typically used: 1.0 milligrams per square inch ("msi") for a beer can, 1.5 msi for a soda can, and 2.2 msi for a can intended for use in packaging a "hard-to-hold" product.

The coated can is filled with this room-temperature conductive solution, and an electrical probe is attached in contact to the outside of the can (uncoated, electrically conducting). A second probe is immersed in the salt solution in the middle of the inside of the can.

If any uncoated metal is present on the inside of the can, a current is passed between these two probes and registers as a value on an LED display of a suitable measurement apparatus. The LED displays the conveyed currents in milliamps (mA). The current that is passed is directly proportional to the amount of metal that has not been effectively covered with coating. The goal is to achieve 100% coating coverage on the inside of the can, which would result in an LED reading of 0.0 mA. Preferred coatings should give metal exposure values of less than 3 mA, more preferred values of less than 2 mA, and even more preferred values of less than 1 mA. Commercially acceptable metal exposure values are typically less than 2.0 mA on average.

Metal Exposure After Drop Damage Test. Drop damage resistance measures the ability of the coated container to resist cracks after being in conditions simulating dropping of a filled can. The presence of cracks is measured by passing electrical current via an electrolyte solution, as previously described in the Initial Metal Exposure section. A coated container is filled with the electrolyte solution (1% NaCl in deionized water) and the initial metal exposure is recorded. The electrolyte solution is removed and the can is then filled with room-temperature tap water. For two-piece "inside spray" beverage cans, the film weights described in the Initial Metal Exposure test can be used.

The water-filled can, which does not include a "top" can end, is dropped through a cylindrical tube having a 2 and ⅞ inch internal diameter, can bottom down, onto an impact wedge (e.g., an inclined plane angled upwards at 45 degrees). The impact wedge is positioned relative to the tube such that a dent is formed in the rim area where the can bottom end meets the sidewall (typically referred to as the "chime" of a beverage can). The water-filled can is dropped through the tube from a 24-centimeter height (as measured between the can bottom and the point of impact on the impact wedge) onto an inclined plane, causing a dent in the chime area. The can is then turned 180 degrees, and the process is repeated.

Water is then removed from the can and metal exposure is again measured as described above. If there is no damage, no change in current (mA) will be observed relative to the Initial Metal Exposure value. Typically, an average of 6 or 12 container runs is recorded. The metal exposure results for before and after the drop are reported as absolute values. The lower the milliamp value, the better the resistance of the coating to drop damage. Preferred coatings should give metal exposure values after drop damage of less than 3.5 mA, more preferred values of less than 2.5 mA, and even more preferred values of less than 1.5 mA.

EXAMPLES

Example 1

In Example 1, an oxirane-functional vinyl monomer was prepared from vanillyl alcohol.

In a first step, 100 g (0.65 mol) of vanillyl alcohol was mixed with 14.8 g (0.065 mol) of benzyl triethyl ammonium chloride (TEBAC) and 300 g (3.24 mol) of epichlorohydrin in a glass vessel. The reaction mixture was stirred for 8 hours at 30° C. 200 g of dichloromethane was added to the mixture, and the mixture was washed with NaCl-saturated water. The organic phase was dried with anhydrous sodium sulphate and filtered. After filtration, the solvent and the unreacted epichlorohydrin were removed by vacuum distillation at 70° C. and 0.01 mbar.

In a second step, the product obtained at the end of the first step was dissolved in 200 g of dichloromethane, and mixed with 104 g of demineralized water, 25.95 g (0.65 mol) sodium hydroxide, and 6.8 g (0.032 mol) of tetraethylammonium bromide. The mixture was vigorously stirred for 3 hours at room temperature (about 25° C.). After decantation, the organic phase was washed twice with NaCl-saturated water. The organic phase was dried, and the solvents were removed by vacuum distillation at 70° C. and 0.01 mbar. After drying, 130 g of a white crystalline product was isolated and identified by NMR as being vanillyl alcohol mono glycidyl ether. The NMR spectrum is shown in FIG. 1A.

The yield of the vanillyl alcohol glycidyl ether can be calculated as a percentage of a theoretical yield. In theory, one mole of vanillyl alcohol (having a molecular weight of 154 g/mol) produces one mole of vanillyl alcohol glycidyl ether (having a molecular weight of 209 g/mol). Thus, in theory, 100 g of vanillyl alcohol produces 135 g of vanillyl alcohol glycidyl ether. The calculated yield achieved in this example is 130 g/135 g=96%.

Figure 1B:
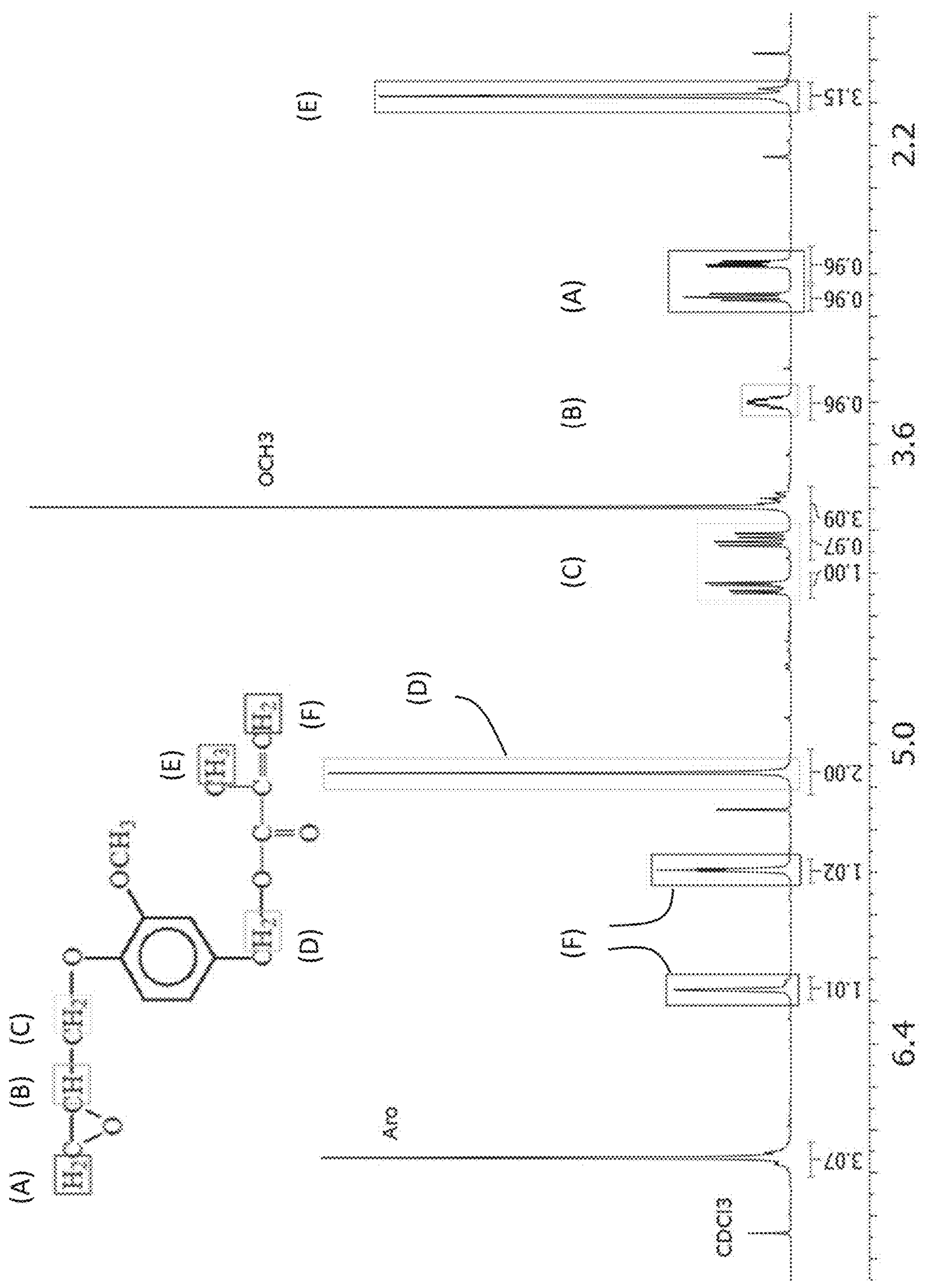
FIG. 1B is an NMR spectrum of a sample in Example 1.

In a third step, 130 g (0.62 mol) of vanillyl alcohol glycidyl ether from the second step, 300 g of dichloromethane, 100.1 g (0.65 mol) of methacrylic anhydride, and 3.97 g 4-dimethylaminopyridine (DMAP) were mixed for 8 hours at 30° C. Then a 1M solution of sodium hydroxide was added and the mixture was vigorously stirred for 4 hours. After separation, the addition of sodium hydroxide was repeated and finally the organic phase was washed with NaCl-saturated water. After drying with anhydrous sodium sulphate, the solvent was removed by vacuum distillation at 70° C. and 0.01 mbar. 156 g of a white crystalline product was isolated. The white crystalline product was identified as vanillyl alcohol glycidyl methacrylate by NMR. The NMR spectrum is shown in FIG. 1B.

The yield of the vanillyl alcohol glycidyl methacrylate can be calculated as a percentage of a theoretical yield. In theory, one mole of vanillyl alcohol glycidyl ether (having a molecular weight of 209 g/mol) produces one mole of vanillyl alcohol glycidyl methacrylate (having a molecular weight of 277 g/mol). Thus, in theory, 130 g of vanillyl alcohol glycidyl ether produces 172 g of vanillyl alcohol glycidyl methacrylate. The calculated yield achieved in this example is 156 g/172 g=91%.

Example 2

A process of transesterification of vanillyl alcohol glycidyl ether was developed.

In a glass vessel equipped with a water trap and a stirrer, 130 g (0.62 mol) of vanillyl alcohol glycidyl ether, 619 g of methyl methacrylate, and 0.7 g (0.0032 mol) of hydroquinone were loaded. The mixture was heated at 100° C. and water traces were removed by azeotropic distillation. 30 minutes later, 8.8 g (0.018 mol) zirconium acetyl acetonate ("ZrAcac," CAS No. 17501-44-9) was added. The mixture was maintained at 100° C. for 20 hours, while occasionally removing the distillate which contains methanol. The mixture was vacuum distilled at 70° C. and 0.01 mbar. The product was dissolved in methylene chloride and washed with water. After decantation, the solvent was removed by vacuum distillation at 70° C. and 0.01 mbar.

Figure 2:
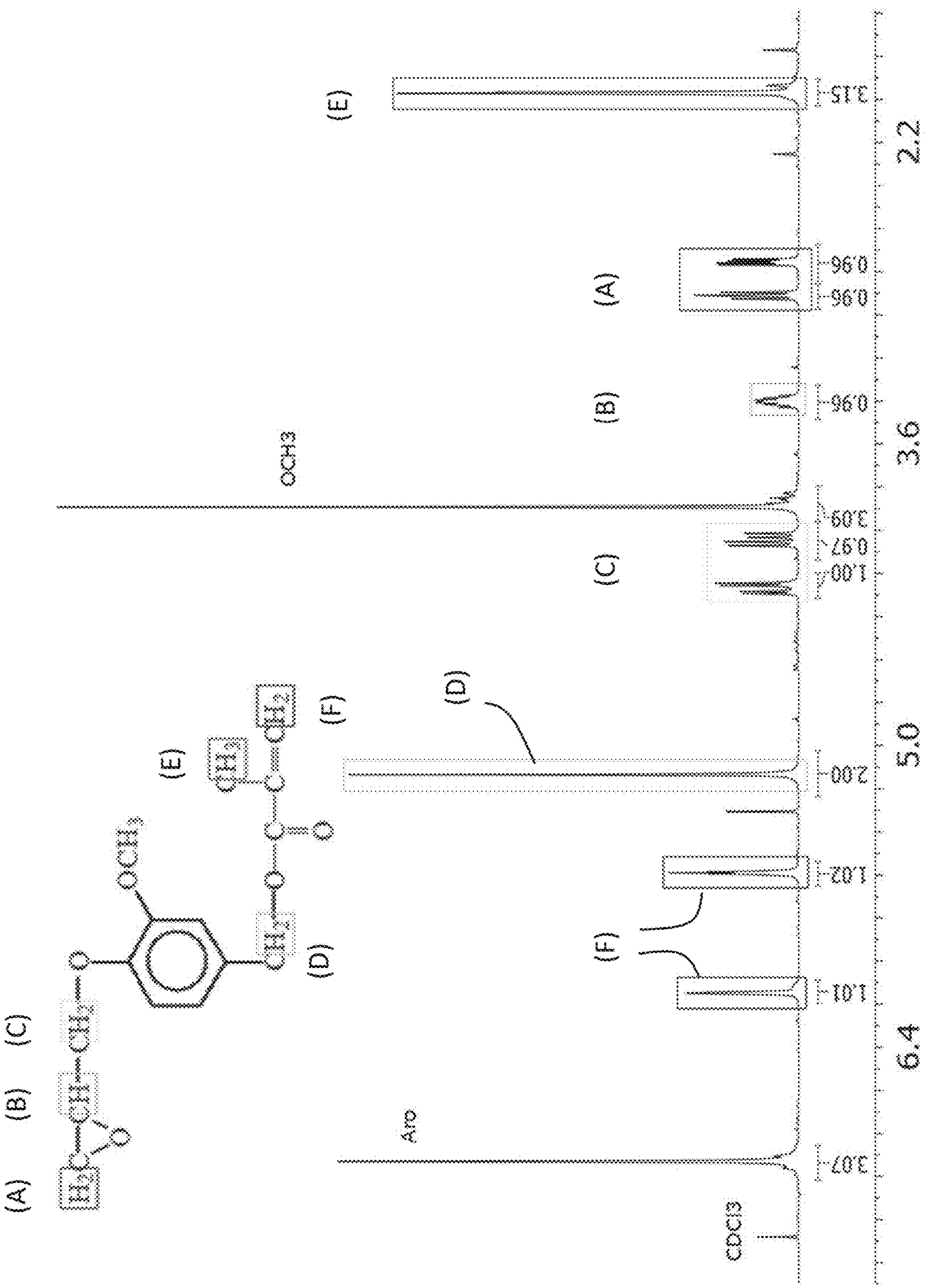
FIG. 2 is an NMR spectrum of a sample in Example 2.

152 g of a crystalline cream product was obtained, providing a yield of 88 wt-% based on the amount of vanillyl alcohol glycidyl ether. The product was identified as vanillyl alcohol glycidyl methacrylate by NMR. The NMR spectrum is shown in FIG. 2.

Examples 3-6

Various copolymers may be prepared from the oxirane-functional vinyl monomer according to the following Examples 3-6. The oxirane-functional vinyl monomer may be, for example, vanillyl alcohol epoxy-methacrylate (VAEM), and may be prepared according to Example 1 or 2.

Example 3

A copolymer may be prepared according to the following method, using the compounds shown in TABLE 1.

TABLE 1

| | Component | Amount (g) | Obtainable from |
|---|---|---|---|
| 1 | Polymerizable surfactant | 18 | Adeka |
| 2 | Deionized water | 790 | |
| 3 | dodecylbenzenesulfonic acid (DDBSA) 72% | 10.2 | Cytec |
| 4 | Ammonium persulfate | 0.5 | Sigma Aldrich |
| 5 | Deionized water | 40 | |
| 6 | Styrene | 144 | Rohm & Haas |
| 7 | Methacrylic acid | 55 | Rohm & Haas |
| 8 | Ethyl acrylate | 37 | Rohm & Haas |
| 9 | Hydroxyethyl methacrylate | 27 | Rohm & Haas |
| 10 | Butylglycol | 20 | Dow Chemicals |
| 11 | Dimethyl ethanol amine | 2.85 | BASF |
| 12 | Deionized water | 40 | |
| 13 | Ferrous sulphate heptahydrate | 0.001 | Sigma Aldrich |
| 14 | t-amyl hydroperoxide | 0.32 | Sigma Aldrich |
| 15 | Deionized water | 10 | |
| 16 | styrene | 144 | Rohm & Haas |
| 17 | VAEM | 96 | According to Example 1 or 2 |
| 18 | Ethyl acrylate | 42 | Rohm & Haas |
| 19 | Hydroxyethyl methacrylate | 11 | Rohm & Haas |
| 20 | Butylglycol | 30 | Dow Chemicals |
| 21 | Isoascorbic acid | 0.24 | Sigma Aldrich |
| 22 | Deionized water | 40 | |
| 23 | Ferrous sulphate heptahydrate | 0.001 | Sigma Aldrich |
| 24 | t-amyl hydroperoxide | 0.3 | Sigma Aldrich |
| 25 | Isoascorbic acid | 0.2 | Sigma Aldrich |
| 26 | Deionized water | 10 | |

In a glass vessel under stirring and nitrogen atmosphere, components 1-3 of TABLE 1 are heated to 80° C. Mixtures containing components 4+5 and 6-10 are added simultaneously via separate input lines over 75 minutes under stirring, while the temperature is maintained at 80° C. After addition the mixture is maintained at 80° C. for 30 minutes under stirring.

Then mixture of components 11+12 is added under stirring over 30 minutes at 80° C. 15 minutes later components 13-15 are added to the reactor. Then the mixtures of 16-20 and 21-22 are added simultaneously via separate input lines over 75 minutes under stirring, while the temperature is maintained at 80° C.

30 minutes later components 23-26 are added to the reactor mixture. The product is maintained under stirring at 80° C. for 90 minutes. After slow cooling at 40° C., the formed latex is filtered.

The non-volatile content of the latex will be 32% and acid value 63.

Example 4

A copolymer may be prepared according to the following method, using the components shown in TABLES 2A-2C. First, an acrylic intermediate may be prepared using the components in TABLE 2A. Then, an acrylic salt may be prepared using the components in TABLE 2B. Finally, a latex may be prepared using the components in TABLE 2C.

TABLE 2A

Acrylic Intermediate.

| | Component | Amount (g) | Obtainable from |
|---|---|---|---|
| 1 | Butanol | 635.8 | Dow Chemicals |
| 2 | Deionized water | 48.1 | |
| 3 | tButyl peroctoate | 16.6 | Akzo Nobel |
| 4 | Butanol | 838.5 | Dow Chemicals |
| 5 | Deionized water | 59.5 | |
| 6 | Methacrylic acid | 802.6 | Rohm & Haas |
| 7 | Ethyl acrylate | 445.9 | Rohm & Haas |
| 8 | Styrene | 535.1 | Rohm & Haas |
| 9 | tButyl peroctoate | 108.6 | Akzo Nobel |
| 10 | tButyl peroctoate | 21.2 | Akzo Nobel |
| 11 | Butanol | 59.2 | Dow Chemicals |
| 12 | tButyl peroctoate | 4.6 | Akzo Nobel |

Components 1-2 of TABLE 2A are heated in a glass vessel under stirring and nitrogen atmosphere at 94° C. Component 3 is added and the mixture is held at 94° C. for 5 minutes under stirring. A premix of components 4-9 is added over 2.5 hours under stirring, while the temperature is maintained at 94° C.

Then, mixture of components 10-11 is added over a 30 minute period. The batch is held for 30 minutes, then component 12 is added and the batch is held for 2 hours at 94° C. under stirring. After cooling, the resulting acrylic copolymer will have 50% non-volatile content and its acid value will be 303.

TABLE 2B

| | Acrylic Salt. | | |
|---|---|---|---|
| | Component | Amount (g) | Obtainable from |
| 1 | Intermediate acrylic | 1799.2 | TABLE 2A |
| 2 | Deionized water | 2155.9 | |
| 3 | Dimethyl ethanolamine | 158.6 | BASF |
| 4 | Distillate | 1541 | |
| 5 | Deionized water | 1615 | |

Components 2 and 3 of TABLE 2B are added slowly to component 1 in a glass vessel under stirring and nitrogen to reflux, then heated to reflux until 1541 g of distillate is collected. Then component 5 is added to the reactor contents.

After cooling the acrylic copolymer solution will have 22% non-volatile content and acid value 302.

TABLE 2C

| | Latex. | | |
|---|---|---|---|
| | Component | Amount (g) | Obtainable from |
| 1 | Acrylic salt | 1525 | TABLE 2B |
| 2 | Deionized water | 1219.1 | |
| 3 | Styrene | 380.4 | Rohm & Haas |
| 4 | Butyl acrylate | 278.3 | Rohm & Haas |
| 5 | Butyl methacrylate | 194.9 | Rohm & Haas |
| 6 | VAEM | 129 | According to Example 1 or 2 |
| 7 | Benzoin | 9.29 | Sigma Aldrich |
| 8 | Deionized water | 92.9 | |
| 9 | Hydrogen peroxide 35% | 9.29 | Sigma Aldrich |
| 10 | Deionized water | 92.9 | |
| 11 | benzoin | 1.59 | Sigma Aldrich |
| 12 | Deionized water | 92.9 | |
| 13 | Hydrogen peroxide 35% | 1.59 | Sigma Aldrich |
| 14 | Benzoin | 0.52 | Sigma Aldrich |
| 15 | Hydrogen peroxide 35% | 0.52 | Sigma Aldrich |

Components 1-2 of TABLE 2C are heated to 70° C. in a glass vessel under stirring. A premix of components 3-6 is prepared in a separate vessel. At 70° C., 10% of the premix is added, followed by components 7 and 8. The temperature is increased to 79° C., then component 9 is added. 5 minutes later the temperature is adjusted to 81° C. and the remaining premix (components 3-6) is added over one hour. Component 10 is added and the batch is held for 10 minutes. Components 11, 12, and 13 are added, and 45 minutes later components 14 and 15 are added. The batch is held for 2 hours before cooling.

The dispersion will have a solids content of 31.5% and a pH of 7.

Example 5

A copolymer may be prepared according to the following method, using the compounds shown in TABLE 3.

TABLE 3

| | Component | Amount (g) | Obtainable from |
|---|---|---|---|
| 1 | Diethylene glycol diethyl ether | 77 | Dow Chemical |
| 2 | Ethyl methacrylate | 60 | Rohm & Haas |
| 3 | VAEM | 31 | According to Example 1 or 2 |
| 4 | tBu peroxide | 18 | Akzo Nobel |
| 5 | Methyl isobutyl ketone | 135 | Eastman |

Mixture of components 2-4 of TABLE 3 is added to component 1 at 150° C. over a two hour period under stirring and nitrogen atmosphere. The batch is maintained for 3 h at 150-155° C. After this period and while cooling slowly, component 5 is added over 45 minutes.

The resulting acrylic copolymer will have 56% non-volatile content and an epoxy equivalent value measured by titration of 0.14 oxirane eq/100 g.

Example 6

A copolymer may be prepared according to the following method, using the components shown in TABLES 4A-4C. First, an oxirane-functional copolymer may be prepared using the components in TABLE 4A. Then, an acrylic acid copolymer may be prepared using the components in TABLE 4B. Finally, a dispersion may be prepared using the components in TABLE 4C

TABLE 4A

| | Oxirane-functional Copolymer. | | |
|---|---|---|---|
| | Component | Amount (g) | Obtainable from |
| 1 | Butanol | 524.5 | Dow Chemical |
| 2 | Butylglycol | 524.5 | Dow Chemical |
| 3 | tButyl peroctoate | 14.2 | Akzo Nobel |
| 4 | Styrene | 1162 | Rohm & Haas |
| 5 | Hydroxy ethyl methacrylate | 888 | Dow Chemical |
| 6 | VAEM | 112 | According to Example 1 or 2 |
| 7 | tButyl peroctoate | 90.4 | Akzo Nobel |
| 8 | Butylglycol | 43 | Dow Chemical |
| 9 | tButyl peroctoate | 45.1 | Akzo Nobel |
| 10 | Butylglycol | 105 | Dow chemical |
| 11 | Butylglycol | 27 | Dow chemical |
| 12 | tButyl peroctoate | 4.34 | Akzo Nobel |
| 13 | tButyl peroctoate | 4.34 | Akzo Nobel |
| 14 | tButyl peroctoate | 4.34 | Akzo Nobel |

Components 1-2 of TABLE 4A are heated under stirring and nitrogen atmosphere at 98° C. Component 3 is added. Five minutes later, a mixture of components 4-7 is added under stirring at 97-101° C. over 2.5 hours. After addition, component 8 is added, followed by the addition of a mixture of components 9-10 over one hour. Component 11 is added and the batch is held for one hour at 97 to 99° C. Then component 12 is added, and one hour later component 13 and another hour later component 14 is added. The batch is held for one hour at 97 to 99° C.

After cooling, the composition will have 62% non-volatile content and an epoxy equivalent value of 0.02 oxirane eq per 100 g solid resin.

TABLE 4B

Acrylic Acid Copolymer.

| | Component | Amount (g) | Obtainable from |
|---|---|---|---|
| 1 | Butanol | 129.6 | Dow Chemical |
| 2 | Deionized water | 9.8 | |
| 3 | Methacrylic acid | 163.6 | Arkema |
| 4 | Butyl methacrylate | 163.6 | Arkema |
| 5 | Styrene | 36.4 | Lyondell |
| 6 | Benzoyl peroxide (70% in water) | 23.4 | Akzo Nobel |
| 7 | Butanol | 183 | Dow Chemical |
| 8 | Deionized water | 12.2 | |

To components 1-2 of TABLE 4B, under stirring and nitrogen atmosphere, 10% of a mixture of components 3-6 is added. The temperature is increased to 93° C. and heating is stopped. About 15 minutes later, the temperature is increased to 97° C. The remaining 90% of the mixture of components 3-6 is added to a mixture of components 7 and 8, and this mixture is added to the reaction vessel over 2 hours. The temperature is maintained at 97 to 99° C. for two hours. Butyl glycol may be added to adjust the non-volatile content to 44.5-50%.

TABLE 4C

Dispersion.

| | Component | Amount (g) | Obtainable from |
|---|---|---|---|
| 1 | Oxirane copolymer | 894.6 | TABLE 4A |
| 2 | Acrylic acid copolymer | 277.3 | TABLE 4B |
| 3 | Deionized water | 13.7 | |
| 4 | Dimethyl ethanol amine | 30.3 | BASF |
| 5 | Deionized water | 1036 | |

Component 3 of TABLE 4C is added to a mixture of components 1 and 2. The temperature of the mixture is progressively increased to 99° C. Then component 4 is added over 5 minutes. The batch is held for 4 hours at 97 to 99° C. Then heating is stopped and component 5 is added under high agitation over 1 hour and 15 minutes, while the temperature is allowed to decrease.

the resulting dispersion will have 30% non-volatile content, a pH of 6.8, and a particle size of 0.25 μm.

Exemplary Embodiments

Embodiment 1 is a method for making a monomer, the method comprising:

reacting an alkanol-substituted phenol with epihalohydrin in the presence of a phase transfer catalyst (preferably a quaternary ammonium salt or quaternary phosphonium salt) at a temperature of 50° C. or lower to produce a first intermediate product;

removing excess epihalohydrin;

after removing excess epihalohydrin, contacting the first intermediate product with a base to produce a second intermediate product; and forming an oxirane-functional vinyl monomer from the second intermediate product.

Embodiment 2 is the method of embodiment 1, wherein the alkanol-substituted phenol comprises a compound of Formula (I):

Formula (I)

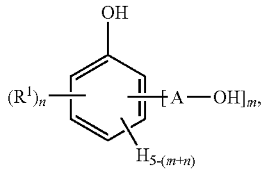

wherein A is a carbon-containing linkage group, preferably $—[C(R^2)_2]_h—$, more preferably $—C(R^2)_2—$, most preferably $—CH_2—$, wherein each $R^2$ is independently selected from H or a carbon-containing group, preferably H or an alkyl or alkoxy group, preferably wherein the alkyl or alkoxy group has 1 to 4 carbon atoms, more preferably wherein the alkyl or alkoxy group has a single carbon atom, most preferably wherein $R^2$ is H, wherein h is 1 or greater, preferably h is 1 to 10, more preferably 1 to 6, and even more preferably 1 to 4, wherein each $R^1$ is independently a carbon-containing group, preferably an alkyl or alkoxy, preferably wherein $R^1$ has 1 to 4 carbon atoms, most preferably wherein $R^1$ has a single carbon atom, optionally wherein two or more of $R^1$ and/or A can join to form one or more cyclic groups (e.g., one or more aromatic rings fused to the depicted phenolic ring), wherein n is 0 to 4, preferably wherein n is 1, and wherein m is 1 to 3, preferably wherein m is 1.

Embodiment 3 is the method of embodiment 1 or 2, wherein the alkanol-substituted phenol comprises a compound of Formula (IA):

Formula (IA)

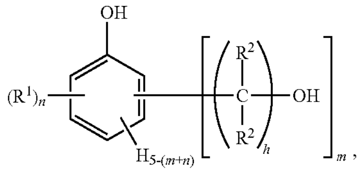

wherein each $R^1$ is independently a carbon-containing group, preferably an alkyl or alkoxy, preferably wherein $R^1$ has 1 to 4 carbon atoms, most preferably wherein $R^1$ has a single carbon atom, wherein n is 0 to 4, preferably wherein n is 1, wherein each $R^2$ is independently selected from H or a carbon-containing group, preferably H or an alkyl or alkoxy group, preferably wherein the alkyl or alkoxy group has 1 to 4 carbon atoms, more preferably wherein the alkyl or alkoxy group has a single carbon atom, most preferably wherein $R^2$ is H, h is 1 or greater, preferably h is 1 to 10, more preferably 1 to 6, and even more preferably 1 to 4, and wherein m is 1 to 3, preferably wherein m is 1.

Embodiment 4 is the method of embodiment 1, 2, or 3, wherein the alkanol-substituted phenol comprises a compound of Formula (IB):

Formula (IB)

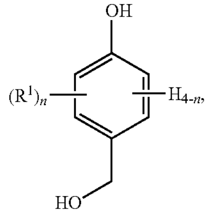

wherein each $R^1$ is independently a carbon-containing group, preferably an alkyl or alkoxy, preferably wherein $R^1$ has 1 to 4 carbon atoms, most preferably wherein $R^1$ has a single carbon atom, and wherein n is 0 to 4.

Embodiment 5 is the method of any one of embodiments 2 to 4, wherein at least one of $R^1$ is methoxy (e.g., at an ortho position relative to the phenolic hydroxyl group) and n is 1 to 4.

Embodiment 6 is the method of embodiment 2 or 3, wherein the phenolic hydroxyl group and the -[A-OH]$_m$ group are in a para position, an ortho position, or a meta position with respect to one another, preferably in a para position.

Embodiment 7 is the method of any one of embodiments 1 to 6, wherein the alkanol-substituted phenol comprises vanillyl alcohol.

Embodiment 8 is the method of any one of embodiments 1 to 7 comprising combining 1 mol part of alkanol-substituted phenol with 1 mol part or more, 2 mol parts or more, 3 mol parts or more, 4 mol parts or more, or preferably 5 mol parts or more of epihalohydrin.

Embodiment 9 is the method of any one of embodiments 1 to 8 comprising combining 1 mol part of alkanol-substituted phenol with 20 mol part or less, 15 mol parts or less, 10 mol parts or less, or preferably 8 mol parts or less of epihalohydrin.

Embodiment 10 is the method of any one of embodiments 1 to 9 comprising combining 1 mol part of alkanol-substituted phenol with 1/1000 mol part or more, 1/100 mol part or more, 1/50 mol part or more, 1/20 mol part or more, or preferably 1/10 mol part or more of the phase transfer catalyst, wherein the phase transfer catalyst preferably comprises a quaternary salt, more preferably a quaternary ammonium salt or a quaternary phosphonium salt, most preferably a quaternary ammonium salt.

Embodiment 11 is the method of any one of embodiments 1 to 10 comprising combining 1 mol part of alkanol-substituted phenol with ½ mol part or less or preferably 1/5 mol parts or less of the phase transfer catalyst, wherein the phase transfer catalyst preferably comprises a quaternary salt, more preferably a quaternary ammonium salt or a quaternary phosphonium salt, most preferably a quaternary ammonium salt.

Embodiment 12 is the method of any one of embodiments 1 to 11, wherein the base is water soluble.

Embodiment 13 is the method of any one of embodiments 1 to 12, wherein the base comprises a metallic base (e.g., a base including aluminum, calcium, lithium, magnesium, sodium, or potassium), preferably a metal hydroxide, more preferably NaOH.

Embodiment 14 is the method of any one of embodiments 1 to 13 comprising combining 1 mol part of the first intermediate product with 1 mol part or more, 2 mol parts or more, 3 mol parts or more, 4 mol parts or more, or 5 mol parts or more of a base, preferably a metallic base (e.g., a base including aluminum, calcium, lithium, magnesium, sodium, or potassium), more preferably NaOH.

Embodiment 15 is the method of any one of embodiments 1 to 14 comprising combining 1 mol part of the first intermediate product with 10 mol parts or less, 8 mol parts or less, 5 mol parts or less, or 3 mol parts or less of a base, preferably a metallic base (e.g., a base including aluminum, calcium, lithium, magnesium, sodium, or potassium), more preferably NaOH.

Embodiment 16 is the method of any one of embodiments 1 to 15, wherein the first intermediate product comprises a halohydrin ether of alkanol-substituted phenol.

Embodiment 17 is the method of embodiment 16, wherein the halohydrin ether of alkanol-substituted phenol comprises a compound of Formula (II):

Formula (II)

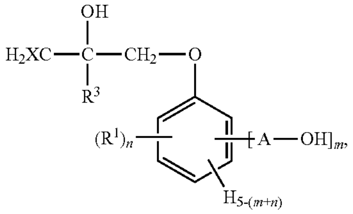

wherein A, $R^1$, m, and n are as in Embodiment 2, $R^3$ is H or an alkyl, preferably wherein $R^3$ is H, and wherein X is a halogen, preferably Cl.

Embodiment 18 is the method of embodiment 16 or 17, wherein the halohydrin ether of alkanol-substituted phenol comprises a compound of Formula (IIA):

Formula (IIA)

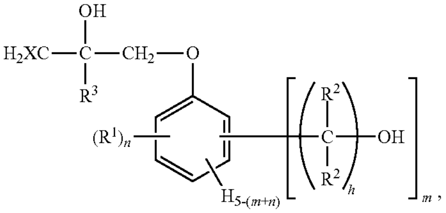

wherein $R^1$, $R^2$, h, m, and n are as in Embodiment 2, $R^3$ is H or an alkyl, preferably wherein $R^3$ is H, and wherein X is a halogen, preferably Cl.

Embodiment 19 is the method of embodiment any one of embodiments 16 to 18, wherein the first intermediate product comprises a mixture of a mono-epoxide glycidyl ether of alkanol-substituted phenol and halohydrin ether of alkanol-substituted phenol.

Embodiment 20 is the method of any one of embodiments 16 to 19, wherein the halohydrin ether of alkanol-substituted phenol has a yield of 60 wt-% or more, 70 wt-% or more, 80 wt-% or more, or 90 wt-% or more.

Embodiment 21 is the method of any one of embodiments 1 to 20, wherein the contacting of the first intermediate product with the base occurs in the presence of an organic solvent.

Embodiment 22 is the method of any one of embodiments 1 to 21, wherein forming of the second intermediate product occurs substantially at 50° C. or lower.

Embodiment 23 is the method of any one of embodiments 1 to 22, wherein the second intermediate product comprises mono-epoxide glycidyl ether of alkanol-substituted phenol.

Embodiment 24 is the method of any one of embodiments 1 to 23, wherein the second intermediate product comprises 70 wt-% or more, 80 wt-% or more, or 90 wt-% or more of mono-epoxide glycidyl ether of alkanol-substituted phenol.

Embodiment 25 is the method of any one of embodiments 1 to 24, wherein the mono-epoxide glycidyl ether of alkanol-substituted phenol has a yield of 70 wt-% or more, 80 wt-% or more, or 90 wt-% or more.

Embodiment 26 is the method of any one of embodiments 1 to 25 further comprising washing the first intermediate product, the second intermediate product, the oxirane-functional vinyl monomer, or a combination thereof.

Embodiment 27 is the method of any one of embodiments 1 to 26, wherein the second intermediate product has an epoxy equivalent weight of 150 or greater, 175 or greater, 180 or greater, or 200 or greater, preferably 175 or greater.

Embodiment 28 is the method of any one of embodiments 1 to 27, wherein the contacting of the first intermediate product with the base further comprises contacting with a phase transfer catalyst (preferably an ammonium salt or phosphonium salt, most preferably a quaternary ammonium salt or quaternary phosphonium salt).

Embodiment 29 is the method of any one of embodiments 1 to 28, wherein removing excess epihalohydrin comprises distillation.

Embodiment 30 is the method of any one of embodiments 1 to 29, wherein less than 1 wt-% of epihalohydrin remains in a reaction mixture after the removing of the excess epihalohydrin.

Embodiment 31 is the method of any one of embodiments 1 to 30, wherein less than 50 ppm of epihalohydrin remains in a reaction mixture after forming of the oxirane-functional vinyl monomer.

Embodiment 32 is the method of any one of embodiments 1 to 31, wherein the epihalohydrin comprises epichlorohydrin.

Embodiment 33 is the method of any one of embodiments 1 to 32, wherein the oxirane-functional vinyl monomer comprises a compound of Formula (III):

Formula (III)

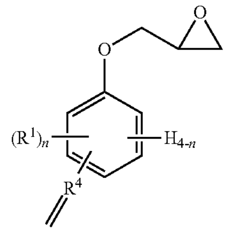

wherein each $R^1$ is independently a carbon-containing group, preferably an alkyl or alkoxy, preferably wherein $R^1$ has 1 to 4 carbon atoms, most preferably wherein $R^1$ has a single carbon atom;

wherein n is 0 to 4, preferably wherein n is 1; and wherein $R^4$ is a carbon-containing group, optionally wherein $R^4$ contains oxygen, optionally wherein $R^4$ contains an aromatic linkage group, preferably wherein $R^4$ forms part of an acrylate group, most preferably wherein $R^4$ forms part of a methacrylate group.

Embodiment 34 is the method of any one of embodiments 1 to 33, wherein the oxirane-functional vinyl monomer comprises vanillyl alcohol epoxy-methacrylate (VAEM) of Formula (IIID):

Formula (IIID)

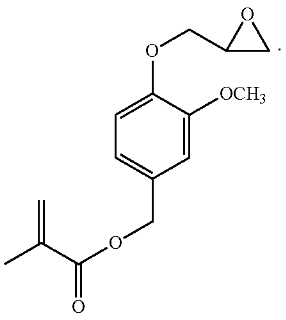

Embodiment 35 is the method of any one of embodiments 1 to 34, wherein the oxirane-functional vinyl monomer has a yield of 50 wt-% or more, 60 wt-% or more, 70 wt-% or more, 80 wt-% or more, or 85 wt-% or more based on a starting amount of the alkanol-substituted phenol reacted with the epihalohydrin.

Embodiment 36 is the method of embodiment 35, wherein the method does not include a chromatographic separation step.

Embodiment 37 is the method of any one of embodiments 1 to 36, wherein the forming of the oxirane-functional vinyl monomer from the second intermediate product comprises (meth)acrylation, nucleophilic substitution with halogen functional vinyl compound, or by transesterification of an itaconic ester.

Embodiment 38 is the method of any one of embodiments 1 to 37, wherein the forming of the oxirane-functional vinyl monomer from the second intermediate product comprises (meth)acrylation by reaction with methacrylic anhydride or transesterification of (meth)acrylic ester.

Embodiment 39 is an oxirane-functional vinyl monomer made by the method of any one of embodiments 1 to 38.

Embodiment 40 is a monomer composition comprising 80 wt-% or more of a compound of Formula (III):

Formula (III)

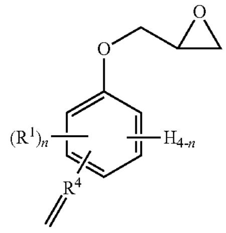

wherein each $R^1$ is independently a carbon-containing group, preferably an alkyl or alkoxy, preferably wherein $R^1$ has 1 to 4 carbon atoms, most preferably wherein $R^1$ has a single carbon atom;

wherein n is 0 to 4, preferably wherein n is 1; and wherein $R^4$ is a carbon-containing group, optionally wherein $R^4$ contains oxygen, optionally wherein $R^4$ contains an aromatic linkage group, preferably wherein $R^4$ forms part of an acrylate group, most preferably wherein $R^4$ forms part of a methacrylate group.

Embodiment 41 is the monomer composition of embodiment 40, wherein $R^4$ includes an ether linkage, an ester linkage (of either directionality —C(═O)—O— or —O—C(═O)—), or an aromatic group (e.g., a C6 aromatic ring).

Embodiment 42 is the monomer composition of embodiment 40 or 41, wherein the compound comprises Formula (IIIA):

Formula (IIIA)

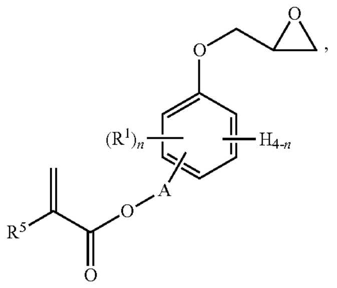

wherein A, $R^1$, m, and n are as in Embodiment 2, and wherein $R^5$ is H or a carbon-containing group, preferably wherein $R^5$ is H or alkyl, most preferably wherein $R^5$ is H or methyl.

Embodiment 43 is the monomer composition of any one of embodiments 40 to 42, wherein the compound comprises Formula (IIIB):

Formula (IIIB)

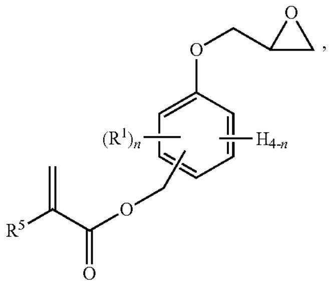

wherein $R^1$ and n are as in Embodiment 2, and wherein $R^5$ is H or a carbon-containing group, preferably wherein $R^5$ is H or alkyl, most preferably wherein $R^5$ is H or methyl.

Embodiment 44 is the monomer composition of any one of embodiments 40 to 43, wherein the compound comprises Formula (IIIC):

Formula (IIIC)

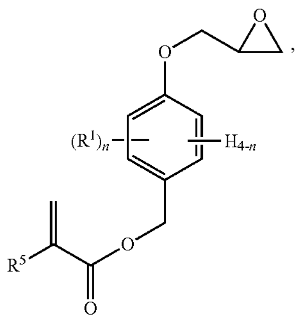

wherein $R^1$ and n are as in Embodiment 2, and wherein $R^5$ is H or a carbon-containing group, preferably wherein $R^5$ is H or alkyl, most preferably wherein $R^5$ is H or methyl.

Embodiment 45 is the monomer composition of any one of embodiments 40 to 44, wherein the compound comprises Formula (IIID):

Formula (IIID)

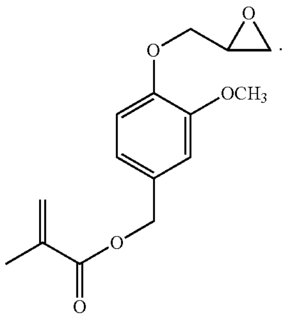

Embodiment 46 is a composition comprising 80 wt-% or more of a mixture of mono-epoxide glycidyl ether of alkanol-substituted phenol and halohydrin ether of alkanol-substituted phenol, measured on a non-volatile basis.

Embodiment 47 is a thermoset coating composition comprising an acrylic copolymer, wherein the acrylic copolymer is formed from reactants comprising the monomer composition of any one of embodiments 40 to 46.

Embodiment 48 is the thermoset coating composition of embodiment 47 wherein the oxirane-functional vinyl monomer of any preceding embodiment (e.g., the oxirane-functional vinyl monomer of any of compounds of Formula III, IIIA, IIIB, IIIC, or IIID) constitutes 1 wt-% or more, 2 wt-% or more, 5 wt-% or more, or 10 wt-% or more of the acrylic copolymer.

Embodiment 49 is the thermoset coating composition of embodiment 47 or 48, wherein the oxirane-functional vinyl monomer of any preceding embodiment (e.g., the oxirane-functional vinyl monomer of any of compounds of Formula III, IIIA, IIIB, IIIC, or IIID) constitutes 90 wt-% or less, 75 wt-% or less, 50 wt-% or less, 30 wt-% or less, 20 wt-% or less, or 10 wt-% or less of the acrylic copolymer.

Embodiment 50 is the thermoset coating composition of any one of embodiments 47 to 49, wherein the acrylic copolymer comprises an emulsion polymerized latex polymer.

Embodiment 51 is the thermoset coating composition of any one of embodiments 47 to 50, wherein the emulsion polymerized latex polymer is formed by emulsion polymerizing an ethylenically unsaturated monomer mixture including an oxirane-functional vinyl monomer of any preceding embodiment in the presence of a salt of an acid- or anhydride-functional polymer (e.g., a salt of an acid- or anhydride-functional organic solution polymerized acrylic copolymer), polyester polymer (e.g., a salt of an acid or anhydride-functional polyester-acrylic copolymer), or polyether polymer (e.g., a salt of an acid or anhydride-functional polyether-acrylic copolymer).

Embodiment 52 is the thermoset coating composition of any one of embodiments 47 to 51, wherein the acrylic copolymer comprises an organic solution polymerized polymer Embodiment 53 is the thermoset coating composition of any one of embodiments 47 to 52, wherein the acrylic copolymer comprises a reaction product of an amine (preferably a tertiary amine), an oxirane-functional acrylic copolymer and an acid-functional polymer.

Embodiment 54 is the thermoset coating composition of any one of embodiments 47 to 53, wherein the acrylic copolymer has a calculated Tg of 0° C. or more, 20° C. or more, 40° C. or more, 50° C. or more, 60° C. or more, or 70° C. or more.

Embodiment 55 is the thermoset coating composition of any of embodiments 47 to 54, wherein the coating composition includes 5 wt-% or more, 10 wt-% or more, 20 wt-% or more, 35 wt-% or more, 50 wt-% or more, 65 wt-% or more, 80 wt-% or more, 90 wt-% or more, or 95 wt-% or more, or 99 wt-% or more of the acrylic copolymer, based on total resin solids included in the coating composition.

Embodiment 56 is the thermoset coating composition of any of embodiments 47 to 55, wherein the coating composition includes 100 wt-% or less, 95 wt-% or less, 90 wt-% or less, 80 wt-% or less, 60 wt-% or less, 40 wt-% or less, 20 wt-% or less, 10 wt-% or less of the acrylic copolymer, based on total resin solids included in the coating composition.

Embodiment 57 is the thermoset coating composition of any of embodiments 47 to 56, wherein the coating composition includes a crosslinker (e.g., a phenoplast, an aminoplast, a blocked isocyanate, or a beta-hydroxy alkylamide).

Embodiment 58 is the thermoset coating composition of any of embodiments 47 to 57, wherein the coating composition comprises a solvent-based or aqueous food or beverage can coating composition.

Embodiment 59 is a food or beverage container, or a portion thereof, having a metal substrate and coating disposed on at least a portion of the metal substrate formed the thermoset coating composition of any of embodiments 47 to 58.

All references and publications cited herein are expressly incorporated herein by reference in their entirety into this disclosure, except to the extent they may directly contradict this disclosure. Although specific embodiments have been illustrated and described herein, it will be appreciated by those of ordinary skill in the art that a variety of alternate and/or equivalent implementations can be substituted for the specific embodiments shown and described without departing from the scope of the present disclosure. It should be understood that this disclosure is not intended to be unduly limited by the illustrative embodiments and examples set forth herein and that such examples and embodiments are presented by way of example only with the scope of the disclosure intended to be limited only by the claims set forth here.

The invention claimed is:

1. A method for making a monomer, the method comprising:

reacting an alkanol-substituted phenol with epihalohydrin in the presence of a phase transfer catalyst at a temperature of 50° C. or lower to produce a first intermediate product;

removing excess epihalohydrin;

after removing excess epihalohydrin, contacting the first intermediate product with a base to produce a second intermediate product; and forming an oxirane-functional vinyl monomer from the second intermediate product.

2. The method of claim 1, wherein the alkanol-substituted phenol comprises a compound of Formula (I):

Formula (I)

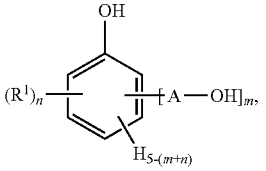

wherein A is a carbon-containing linkage group, wherein each $R^1$ is independently a carbon-containing group, wherein n is 0 to 4, and wherein m is 1 to 3.

3. The method of claim 1, wherein the alkanol-substituted phenol comprises a compound of Formula (IA):

Formula (IA)

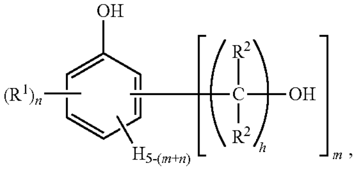

wherein each $R^1$ is independently a carbon-containing group, wherein n is 0 to 4, wherein each $R^2$ is independently selected from H or a carbon-containing group, wherein h is 1 or greater, and wherein m is 1 to 3.

4. The method of claim 1, wherein the alkanol-substituted phenol comprises a compound of Formula (IB):

Formula (IB)

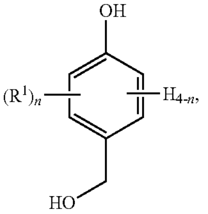

wherein each $R^1$ is independently a carbon-containing group, and wherein n is 0 to 4.

5. The method of claim 2, wherein at least one of $R^1$ is methoxy and n is 1 to 4.

6. The method of claim 1, wherein the base is water soluble, optionally wherein the base comprises a metallic base.

7. The method of claim 1, wherein the first intermediate product comprises a halohydrin ether of alkanol-substituted phenol.

8. The method of claim 7, wherein the halohydrin ether of alkanol-substituted phenol comprises a compound of Formula (II):

Formula (II)

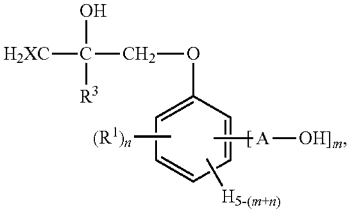

wherein A is a carbon-containing linkage group,
wherein each $R^1$ is independently a carbon-containing group,
wherein n is 0 to 4,
wherein $R^3$ is H or an alkyl, and
wherein X is a halogen.

9. The method of claim 7, wherein the halohydrin ether of alkanol-substituted phenol comprises a compound of Formula (IIA):

Formula (IIA)

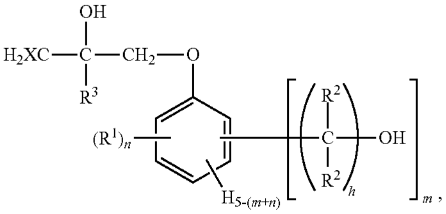

wherein each $R^1$ is independently a carbon-containing group,
wherein each $R^2$ is independently selected from H or a carbon-containing group,
wherein $R^3$ is H or an alkyl,
wherein h is 1 or greater,
wherein m is 1 to 3,
wherein n is 0 to 4, and
wherein X is a halogen.

10. The method of claim 7, wherein the first intermediate product comprises a mixture of a mono-epoxide glycidyl ether of alkanol-substituted phenol and halohydrin ether of alkanol-substituted phenol.

11. The method of claim 1, wherein forming of the second intermediate product occurs substantially at 50° C. or lower.

12. The method of claim 1, wherein the second intermediate product comprises mono-epoxide glycidyl ether of alkanol-substituted phenol.

13. The method of claim 1, wherein the mono-epoxide glycidyl ether of alkanol-substituted phenol has a yield of 70 wt-% or more.

14. The method of claim 1, wherein the contacting of the first intermediate product with the base further comprises contacting with a phase transfer catalyst.

15. The method of claim 1, wherein the oxirane-functional vinyl monomer comprises a compound of Formula (III):

Formula (III)

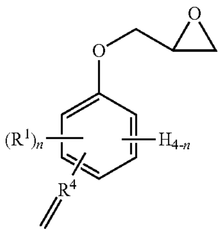

wherein each $R^1$ is independently a carbon-containing group,
wherein n is 0 to 4, and
wherein $R^4$ is a carbon-containing group.

16. The method of claim 1, wherein the oxirane-functional vinyl monomer comprises vanillyl alcohol epoxy-methacrylate (VAEM) of Formula (IIID):

Formula (IIID)

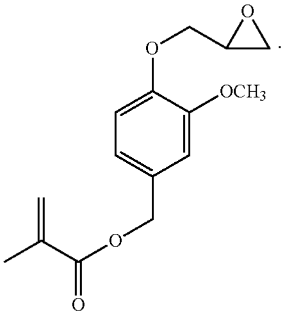

17. The method of claim 1, wherein the oxirane-functional vinyl monomer has a yield of 50 wt-% or more based on a starting amount of the alkanol-substituted phenol reacted with the epihalohydrin.

18. The method of claim 1, wherein the forming of the oxirane-functional vinyl monomer from the second intermediate product comprises (meth)acrylation (optionally by reaction with methacrylic anhydride or transesterification of (meth)acrylic ester), nucleophilic substitution with halogen functional vinyl compound, or by transesterification of an itaconic ester.

19. The method of claim 2, wherein A is $-[C(R^2)_2]_h-$, wherein each $R^2$ is independently selected from H or a carbon-containing group, and wherein h is 1 or greater.

* * * * *